(12) United States Patent
Morrissey et al.

(10) Patent No.: US 11,957,580 B2
(45) Date of Patent: Apr. 16, 2024

(54) TRANSCATHETER DELIVERY SYSTEM WITH WHEEL ACTUATION

(71) Applicant: St. Jude Medical, Cardiology Division, Inc., St. Paul, MN (US)

(72) Inventors: Michael Shane Morrissey, St. Paul, MN (US); Bruce Edward Frohman, Plymouth, MN (US); Michael William Metz, Minneapolis, MN (US); Janis Paulis Skujins, Minneapolis, MN (US); David John Copeland, Minnetonka, MN (US); Spencer Patrick Brown, Providence, RI (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 300 days.

(21) Appl. No.: 17/097,173

(22) Filed: Nov. 13, 2020

(65) Prior Publication Data

US 2021/0059815 A1    Mar. 4, 2021

Related U.S. Application Data

(62) Division of application No. 15/976,282, filed on May 10, 2018, now Pat. No. 10,898,324.
(Continued)

(51) Int. Cl.
    *A61F 2/24*        (2006.01)
    *A61F 2/95*        (2013.01)

(52) U.S. Cl.
    CPC .......... *A61F 2/2436* (2013.01); *A61F 2/2418* (2013.01); *A61F 2/95* (2013.01); *A61F 2/9517* (2020.05)

(58) Field of Classification Search
CPC .... A61F 2/97; A61F 2/966; A61F 2/95; A61F 2/9517; A61F 2/2418; A61F 2/2436
See application file for complete search history.

(56) References Cited

U.S. PATENT DOCUMENTS 3,657,744 A    4/1972   Ersek
4,275,469 A    6/1981   Gabbay
(Continued)

FOREIGN PATENT DOCUMENTS

AU      2011202175 B1    7/2011
DE      19857887 A1    7/2000
(Continued)

OTHER PUBLICATIONS

Alkhatib, U.S. Appl. No. 13/216,124, filed Aug. 23, 2011, titled "Leaflet Suturing To Commissure Points For Prosthetic Heart Valve".
(Continued)

*Primary Examiner* — Todd J Scherbel
(74) *Attorney, Agent, or Firm* — SLEMAN & LUND LLP

(57) ABSTRACT

A delivery device for a collapsible prosthetic heart valve, the delivery device including an inner shaft, a distal sheath disposed about a portion of the inner shaft and forming a compartment with the inner shaft, the compartment being adapted to receive the prosthetic heart valve, the inner shaft and the distal sheath being movable relative to one another, and a handle including a frame having a longitudinal axis, a proximal end and a distal end, the handle further including a deployment actuator and a hub, each of the deployment actuator and the hub being independently capable of opening and closing the compartment, the hub further including a hub actuator coupled to the inner shaft.

14 Claims, 16 Drawing Sheets

Related U.S. Application Data

(60) Provisional application No. 62/506,251, filed on May 15, 2017.

(56) References Cited

U.S. PATENT DOCUMENTS

| | | |
|---|---|---|
| 4,423,730 A | 1/1984 | Gabbay |
| 4,491,986 A | 1/1985 | Gabbay |
| 4,546,767 A | 10/1985 | Smith |
| 4,759,758 A | 7/1988 | Gabbay |
| 4,922,905 A | 5/1990 | Strecker |
| 5,391,172 A | 2/1995 | Williams et al. |
| 5,409,478 A | 4/1995 | Gerry et al. |
| 5,411,552 A | 5/1995 | Andersen et al. |
| 5,456,667 A | 10/1995 | Ham et al. |
| 5,480,423 A | 1/1996 | Ravenscroft et al. |
| 5,707,376 A | 1/1998 | Kavteladze et al. |
| 5,843,167 A | 12/1998 | Dwyer et al. |
| 5,924,424 A | 7/1999 | Stevens et al. |
| 5,935,163 A | 8/1999 | Gabbay |
| 5,961,549 A | 10/1999 | Nguyen et al. |
| 5,968,068 A | 10/1999 | Dehdashtian et al. |
| 6,077,297 A | 6/2000 | Robinson et al. |
| 6,083,257 A | 7/2000 | Taylor et al. |
| 6,090,140 A | 7/2000 | Gabbay |
| 6,214,036 B1 | 4/2001 | Letendre et al. |
| 6,264,691 B1 | 7/2001 | Gabbay |
| 6,267,783 B1 | 7/2001 | Letendre et al. |
| 6,306,141 B1 | 10/2001 | Jervis |
| 6,368,348 B1 | 4/2002 | Gabbay |
| 6,419,695 B1 | 7/2002 | Gabbay |
| 6,488,702 B1 | 12/2002 | Besselink |
| 6,514,261 B1 | 2/2003 | Randall et al. |
| 6,517,576 B2 | 2/2003 | Gabbay |
| 6,533,810 B2 | 3/2003 | Hankh et al. |
| 6,582,464 B2 | 6/2003 | Gabbay |
| 6,610,088 B1 | 8/2003 | Gabbay |
| 6,623,518 B2 | 9/2003 | Thompson et al. |
| 6,685,625 B2 | 2/2004 | Gabbay |
| 6,719,789 B2 | 4/2004 | Cox |
| 6,730,118 B2 | 5/2004 | Spenser et al. |
| 6,736,845 B2 | 5/2004 | Marquez et al. |
| 6,783,556 B1 | 8/2004 | Gabbay |
| 6,790,230 B2 | 9/2004 | Beyersdorf et al. |
| 6,814,746 B2 | 11/2004 | Thompson et al. |
| 6,830,584 B1 | 12/2004 | Seguin |
| 6,866,669 B2 | 3/2005 | Buzzard et al. |
| 6,869,444 B2 | 3/2005 | Gabbay |
| 6,893,460 B2 | 5/2005 | Spenser et al. |
| 6,908,481 B2 | 6/2005 | Cribier |
| 7,018,406 B2 | 3/2006 | Seguin et al. |
| 7,025,780 B2 | 4/2006 | Gabbay |
| 7,105,016 B2 | 9/2006 | Shiu et al. |
| 7,137,184 B2 | 11/2006 | Schreck |
| 7,160,322 B2 | 1/2007 | Gabbay |
| 7,247,167 B2 | 7/2007 | Gabbay |
| 7,267,686 B2 | 9/2007 | DiMatteo et al. |
| 7,311,730 B2 | 12/2007 | Gabbay |
| 7,326,236 B2 | 2/2008 | Andreas et al. |
| 7,329,278 B2 | 2/2008 | Seguin et al. |
| 7,374,573 B2 | 5/2008 | Gabbay |
| 7,381,218 B2 | 6/2008 | Schreck |
| 7,399,315 B2 | 7/2008 | Iobbi |
| 7,419,501 B2 | 9/2008 | Chiu et al. |
| 7,452,371 B2 | 11/2008 | Pavcnik et al. |
| 7,476,244 B2 | 1/2009 | Buzzard et al. |
| 7,510,572 B2 | 3/2009 | Gabbay |
| RE40,816 E | 6/2009 | Taylor et al. |
| 7,585,321 B2 | 9/2009 | Cribier |
| 7,682,390 B2 | 3/2010 | Seguin |
| 7,731,742 B2 | 6/2010 | Schlick et al. |
| 7,803,185 B2 | 9/2010 | Gabbay |
| 7,846,203 B2 | 12/2010 | Cribier |
| 7,846,204 B2 | 12/2010 | Letac et al. |
| 7,914,569 B2 | 3/2011 | Nguyen et al. |
| 7,967,829 B2 | 6/2011 | Gunderson et al. |
| 7,993,384 B2 | 8/2011 | Wu et al. |
| 8,043,353 B2 | 10/2011 | Kaufmann et al. |
| D648,854 S | 11/2011 | Braido |
| D652,926 S | 1/2012 | Braido |
| D652,927 S | 1/2012 | Braido et al. |
| D653,341 S | 1/2012 | Braido et al. |
| D653,342 S | 1/2012 | Braido et al. |
| D653,343 S | 1/2012 | Ness et al. |
| D654,169 S | 2/2012 | Braido |
| D654,170 S | 2/2012 | Braido et al. |
| 8,353,955 B2 | 1/2013 | Styrc et al. |
| 8,562,663 B2 | 10/2013 | Mearns et al. |
| 8,568,475 B2 | 10/2013 | Nguyen et al. |
| 8,778,019 B2 | 7/2014 | Knippel et al. |
| 8,790,386 B2 | 7/2014 | Dwork |
| 8,814,931 B2 | 8/2014 | Wang et al. |
| 9,060,860 B2 | 6/2015 | Morris et al. |
| 9,675,485 B2 | 6/2017 | Essinger et al. |
| 9,820,877 B2 | 11/2017 | Cummins |
| 9,867,701 B2 | 1/2018 | Morris et al. |
| 9,883,960 B2 | 2/2018 | Cummins et al. |
| 9,974,376 B1 | 5/2018 | Liu |
| 10,064,748 B2 | 9/2018 | Shimoyama |
| 10,213,299 B2 | 2/2019 | Backus et al. |
| 10,292,820 B2 | 5/2019 | Morrissey |
| 2002/0036220 A1 | 3/2002 | Gabbay |
| 2002/0183827 A1 | 12/2002 | Derus et al. |
| 2003/0050694 A1 | 3/2003 | Yang et al. |
| 2003/0130726 A1 | 7/2003 | Thorpe et al. |
| 2003/0144725 A1 | 7/2003 | Lombardi |
| 2003/0191516 A1 | 10/2003 | Weldon et al. |
| 2004/0039436 A1 | 2/2004 | Spenser et al. |
| 2004/0049262 A1 | 3/2004 | Obermiller et al. |
| 2004/0093075 A1 | 5/2004 | Kuehne |
| 2004/0148009 A1 | 7/2004 | Buzzard et al. |
| 2004/0186563 A1 | 9/2004 | Lobbi |
| 2004/0210304 A1 | 10/2004 | Seguin et al. |
| 2004/0260390 A1 | 12/2004 | Sarac et al. |
| 2005/0004583 A1 | 1/2005 | Oz et al. |
| 2005/0027305 A1 | 2/2005 | Shiu et al. |
| 2005/0049667 A1 | 3/2005 | Arbefeuille et al. |
| 2005/0080476 A1 | 4/2005 | Gunderson et al. |
| 2005/0096726 A1 | 5/2005 | Sequin et al. |
| 2005/0137695 A1 | 6/2005 | Salahieh et al. |
| 2005/0137697 A1 | 6/2005 | Salahieh et al. |
| 2005/0149159 A1 | 7/2005 | Andreas et al. |
| 2005/0240254 A1 | 10/2005 | Austin |
| 2005/0256566 A1 | 11/2005 | Gabbay |
| 2006/0008497 A1 | 1/2006 | Gabbay |
| 2006/0074484 A1 | 4/2006 | Huber |
| 2006/0106415 A1 | 5/2006 | Gabbay |
| 2006/0122692 A1 | 6/2006 | Gilad et al. |
| 2006/0142848 A1 | 6/2006 | Gabbay |
| 2006/0167468 A1 | 7/2006 | Gabbay |
| 2006/0173532 A1 | 8/2006 | Flagle et al. |
| 2006/0206202 A1 | 9/2006 | Bonhoeffer et al. |
| 2006/0241744 A1 | 10/2006 | Beith |
| 2006/0259120 A1 | 11/2006 | Vongphakdy et al. |
| 2006/0259136 A1 | 11/2006 | Nguyen et al. |
| 2006/0259137 A1 | 11/2006 | Artof et al. |
| 2006/0265056 A1 | 11/2006 | Nguyen et al. |
| 2006/0276813 A1 | 12/2006 | Greenberg |
| 2006/0282150 A1 | 12/2006 | Olson et al. |
| 2006/0282157 A1 | 12/2006 | Hill et al. |
| 2007/0010876 A1 | 1/2007 | Salahieh et al. |
| 2007/0027534 A1 | 2/2007 | Bergheim et al. |
| 2007/0043435 A1 | 2/2007 | Seguin et al. |
| 2007/0055358 A1 | 3/2007 | Krolik et al. |
| 2007/0067029 A1 | 3/2007 | Gabbay |
| 2007/0073391 A1 | 3/2007 | Bourang et al. |
| 2007/0088431 A1 | 4/2007 | Bourang et al. |
| 2007/0093890 A1 | 4/2007 | Eliasen et al. |
| 2007/0100435 A1 | 5/2007 | Case et al. |
| 2007/0112422 A1 | 5/2007 | Dehdashtian |
| 2007/0156225 A1 | 7/2007 | George et al. |
| 2007/0162100 A1 | 7/2007 | Gabbay |
| 2007/0168013 A1 | 7/2007 | Douglas |
| 2007/0203575 A1 | 8/2007 | Forster et al. |
| 2007/0213813 A1 | 9/2007 | Von Segesser et al. |

(56) References Cited

U.S. PATENT DOCUMENTS

| | | |
|---|---|---|
| 2007/0239271 A1 | 10/2007 | Nguyen |
| 2007/0244545 A1 | 10/2007 | Birdsall et al. |
| 2007/0244552 A1 | 10/2007 | Salahieh et al. |
| 2007/0260301 A1 | 11/2007 | Chuter et al. |
| 2007/0288087 A1 | 12/2007 | Fearnot et al. |
| 2008/0004688 A1 | 1/2008 | Spenser et al. |
| 2008/0009940 A1 | 1/2008 | Cribier |
| 2008/0021552 A1 | 1/2008 | Gabbay |
| 2008/0039934 A1 | 2/2008 | Styrc |
| 2008/0071369 A1 | 3/2008 | Tuval et al. |
| 2008/0082159 A1 | 4/2008 | Tseng et al. |
| 2008/0097595 A1 | 4/2008 | Gabbay |
| 2008/0114452 A1 | 5/2008 | Gabbay |
| 2008/0125853 A1 | 5/2008 | Bailey et al. |
| 2008/0140189 A1 | 6/2008 | Nguyen et al. |
| 2008/0147179 A1 | 6/2008 | Cai et al. |
| 2008/0147182 A1 | 6/2008 | Righini et al. |
| 2008/0147183 A1 | 6/2008 | Styrc |
| 2008/0154355 A1 | 6/2008 | Benichou et al. |
| 2008/0154356 A1 | 6/2008 | Obermiller et al. |
| 2008/0228264 A1 | 9/2008 | Li et al. |
| 2008/0243245 A1 | 10/2008 | Thambar et al. |
| 2008/0255662 A1 | 10/2008 | Stacchino et al. |
| 2008/0262602 A1 | 10/2008 | Wilk et al. |
| 2008/0269878 A1 | 10/2008 | Iobbi |
| 2008/0269879 A1 | 10/2008 | Sathe et al. |
| 2009/0024137 A1 | 1/2009 | Chuter et al. |
| 2009/0054975 A1 | 2/2009 | del Nido et al. |
| 2009/0105798 A1 | 4/2009 | Koch |
| 2009/0112309 A1 | 4/2009 | Jaramillo et al. |
| 2009/0118826 A1 | 5/2009 | Khaghani |
| 2009/0138079 A1 | 5/2009 | Tuval et al. |
| 2009/0287299 A1 | 11/2009 | Tabor et al. |
| 2010/0004740 A1 | 1/2010 | Seguin et al. |
| 2010/0036484 A1 | 2/2010 | Hariton et al. |
| 2010/0049306 A1 | 2/2010 | House et al. |
| 2010/0049313 A1 | 2/2010 | Alon et al. |
| 2010/0082094 A1 | 4/2010 | Quadri et al. |
| 2010/0087907 A1 | 4/2010 | Lattouf |
| 2010/0114305 A1 | 5/2010 | Kang et al. |
| 2010/0121434 A1 | 5/2010 | Paul et al. |
| 2010/0131055 A1 | 5/2010 | Case et al. |
| 2010/0168778 A1 | 7/2010 | Braido |
| 2010/0168839 A1 | 7/2010 | Braido et al. |
| 2010/0174290 A1 | 7/2010 | Wuebbeling et al. |
| 2010/0185277 A1 | 7/2010 | Braido et al. |
| 2010/0191326 A1 | 7/2010 | Alkhatib |
| 2010/0204781 A1 | 8/2010 | Alkhatib |
| 2010/0204785 A1 | 8/2010 | Alkhatib |
| 2010/0217382 A1 | 8/2010 | Chau et al. |
| 2010/0249911 A1 | 9/2010 | Alkhatib |
| 2010/0249923 A1 | 9/2010 | Alkhatib et al. |
| 2010/0286768 A1 | 11/2010 | Alkhatib |
| 2010/0298931 A1 | 11/2010 | Quadri et al. |
| 2011/0029072 A1 | 2/2011 | Gabbay |
| 2011/0208298 A1 | 8/2011 | Tuval et al. |
| 2011/0224678 A1 | 9/2011 | Gabbay |
| 2011/0282425 A1 | 11/2011 | Dwork |
| 2011/0288626 A1 | 11/2011 | Straubinger et al. |
| 2011/0295216 A1 | 12/2011 | Miller |
| 2012/0022635 A1 | 1/2012 | Yamashita |
| 2012/0053574 A1 | 3/2012 | Murray, III et al. |
| 2012/0078352 A1 | 3/2012 | Wang et al. |
| 2012/0197391 A1 | 8/2012 | Alkhatib et al. |
| 2012/0310332 A1 | 12/2012 | Murray et al. |
| 2013/0030520 A1 | 1/2013 | Lee et al. |
| 2013/0131774 A1 | 5/2013 | Nabulsi et al. |
| 2013/0138118 A1 | 5/2013 | Doyle |
| 2013/0231735 A1 | 9/2013 | Deem et al. |
| 2013/0297011 A1 | 11/2013 | Morris et al. |
| 2013/0304179 A1 | 11/2013 | Bialas et al. |
| 2014/0067050 A1 | 3/2014 | Costello et al. |
| 2014/0135909 A1 | 5/2014 | Carr et al. |
| 2014/0343670 A1 | 11/2014 | Bakis et al. |
| 2015/0305867 A1 | 10/2015 | Liu et al. |
| 2017/0056169 A1 | 3/2017 | Johnson et al. |

FOREIGN PATENT DOCUMENTS

| | | |
|---|---|---|
| DE | 20000659 U1 | 5/2001 |
| DE | 10121210 A1 | 11/2002 |
| DE | 202008009610 U1 | 12/2008 |
| EP | 0850607 A1 | 7/1998 |
| EP | 1000590 A1 | 5/2000 |
| EP | 1129744 A1 | 9/2001 |
| EP | 1157673 A2 | 11/2001 |
| EP | 1360942 A1 | 11/2003 |
| EP | 1584306 A1 | 10/2005 |
| EP | 1598031 A2 | 11/2005 |
| FR | 2847800 B1 | 10/2005 |
| JP | 2001504717 A | 4/2001 |
| JP | 2003334254 A | 11/2003 |
| JP | 2004130074 | 4/2004 |
| JP | 2010504820 A | 2/2010 |
| JP | 2010526609 A | 8/2010 |
| JP | 2010531193 | 9/2010 |
| JP | 2012500665 A | 1/2012 |
| WO | 9117720 A1 | 11/1991 |
| WO | 9716133 A1 | 5/1997 |
| WO | 9832412 A2 | 7/1998 |
| WO | 9913801 A1 | 3/1999 |
| WO | 0018330 A1 | 4/2000 |
| WO | 0069368 A2 | 11/2000 |
| WO | 0128459 A1 | 4/2001 |
| WO | 200149213 A3 | 7/2001 |
| WO | 0154625 A1 | 8/2001 |
| WO | 0156500 A2 | 8/2001 |
| WO | 2001076510 A2 | 10/2001 |
| WO | 0236048 A1 | 5/2002 |
| WO | 0247575 A2 | 6/2002 |
| WO | 03047468 A1 | 6/2003 |
| WO | 06073626 A2 | 7/2006 |
| WO | 07071436 A2 | 6/2007 |
| WO | 2008042266 A2 | 4/2008 |
| WO | 08070797 A2 | 6/2008 |
| WO | 2008138584 A1 | 11/2008 |
| WO | 2009001309 | 12/2008 |
| WO | 2009011866 A1 | 1/2009 |
| WO | 2009029199 A1 | 3/2009 |
| WO | 2009042196 A2 | 4/2009 |
| WO | 2009091509 A1 | 7/2009 |
| WO | 2010008548 A2 | 1/2010 |
| WO | 2010008549 A1 | 1/2010 |
| WO | 2010051025 A1 | 5/2010 |
| WO | 2010087975 A1 | 8/2010 |
| WO | 2010096176 A1 | 8/2010 |
| WO | 2010098857 A1 | 9/2010 |
| WO | 2011137531 A9 | 11/2011 |
| WO | 2012026965 A2 | 3/2012 |
| WO | 2012036741 A2 | 3/2012 |
| WO | 2016059084 A2 | 4/2016 |

OTHER PUBLICATIONS

Australian Examination Report for Application No. 2011293898 dated Jul. 26, 2013.

Extended European Search Report for U.S. Appl. No. 16/196,712 dated May 9, 2017.

International Search Report and Written Opinion for Application No. PCT/US2011/001450 dated Mar. 5, 2012.

International Search Report and Written Opinion for Application No. PCT/US2011/001615 dated Jul. 11, 2012.

International Search Report and Written Opinion for Application No. PCT/US2013/039407 dated Feb. 10, 2014.

International Search Report and Written Opinion for Application No. PCT/US2014/064253 dated Feb. 3, 2015.

International Search Report and Written Opinion for PCT/US2018/031973, dated Oct. 19, 2018.

International Search Report Application No. PCT/US2011/048963, dated Dec. 15, 2011.

(56) References Cited

OTHER PUBLICATIONS

International Search Report Application No. PCT/US2011/048967, dated Dec. 15, 2011.
International Search Report Application No. PCT/US2011/048989, dated Dec. 15, 2011.
International Search Report for Application No. PCT/US2011/001450 dated Mar. 5, 2012.
International Search Report for Application No. PCT/US2011/001597 dated Mar. 7, 2012.
International Search Report for Application No. PCT/US2011/001615 dated Jul. 11, 2012.
International Search Report for Application No. PCT/US2013/039407 dated Feb. 10, 2014.
International Search Report for Application No. PCT/US2014/064253 dated Feb. 3, 2015.
International Search Report for PCT/US2017/063899, dated Feb. 7, 2018, 3 pages.
International Search Report from PCT/US2017/063893, dated Feb. 7, 2018, 3 pages.
Japanese Office Action for Application No. 2013-525891 dated May 8, 2015.
Knippel, U.S. Appl. No. 13/234,782, filed Sep. 16, 2011, titled "Staged Deployment Devices And Method For Transcatheter Heart Valve Delivery".
Morris, U.S. Appl. No. 13/788,820, filed Mar. 7, 2013, titled "Devices And Methods For Transcatheter Heart Valve Delivery".
Ruiz, Carlos, Overview of PRE-CE Mark Transcatheter Aortic Valve Technologies, Euro PCR, dated May 25, 2010.
Wang, U.S. Appl. No. 13/212,442, filed Aug. 18, 2011, titled "Staged Deployment Devices And Methods For Transcatheter Heart Valve Delivery Systems".

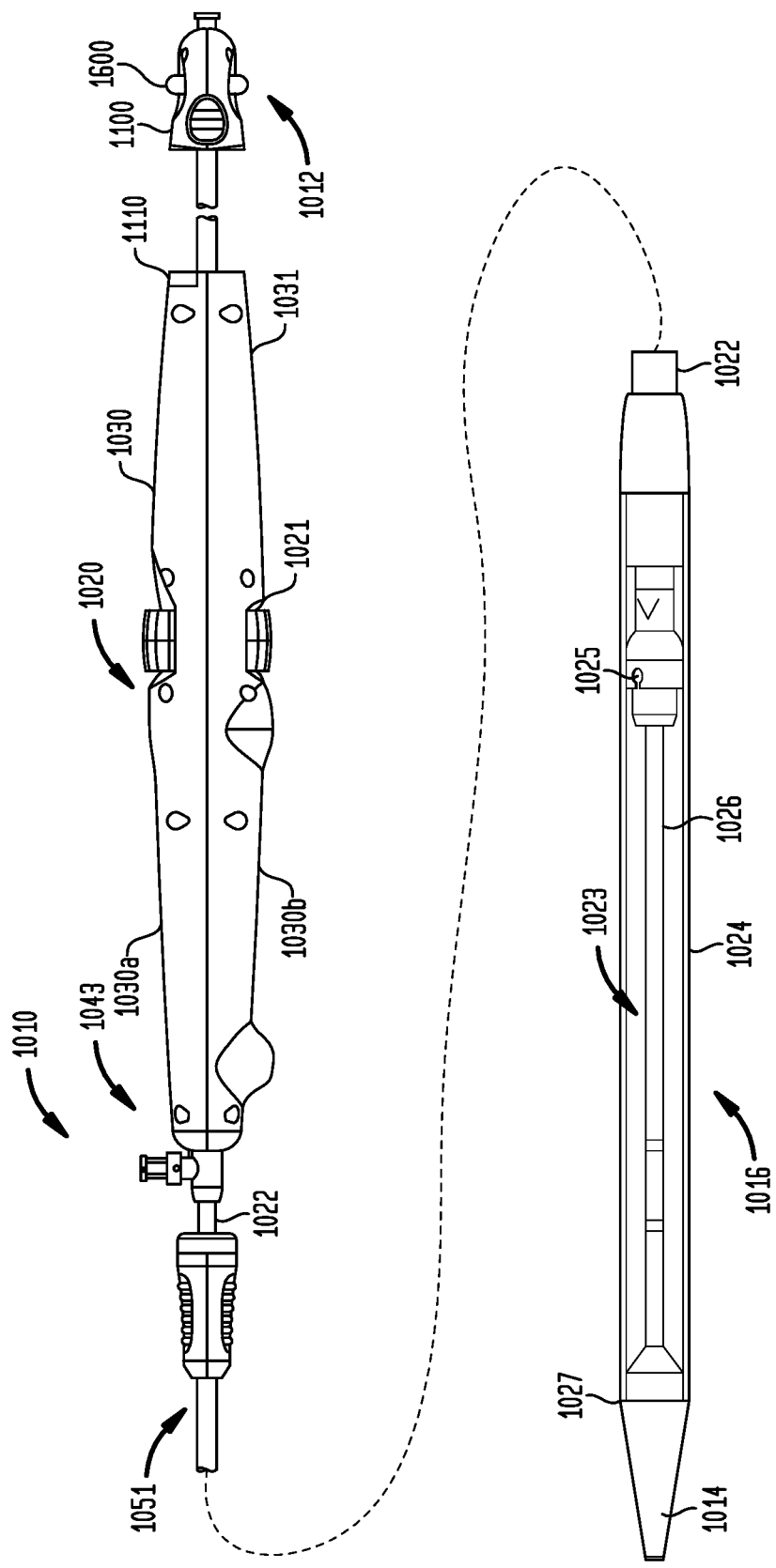

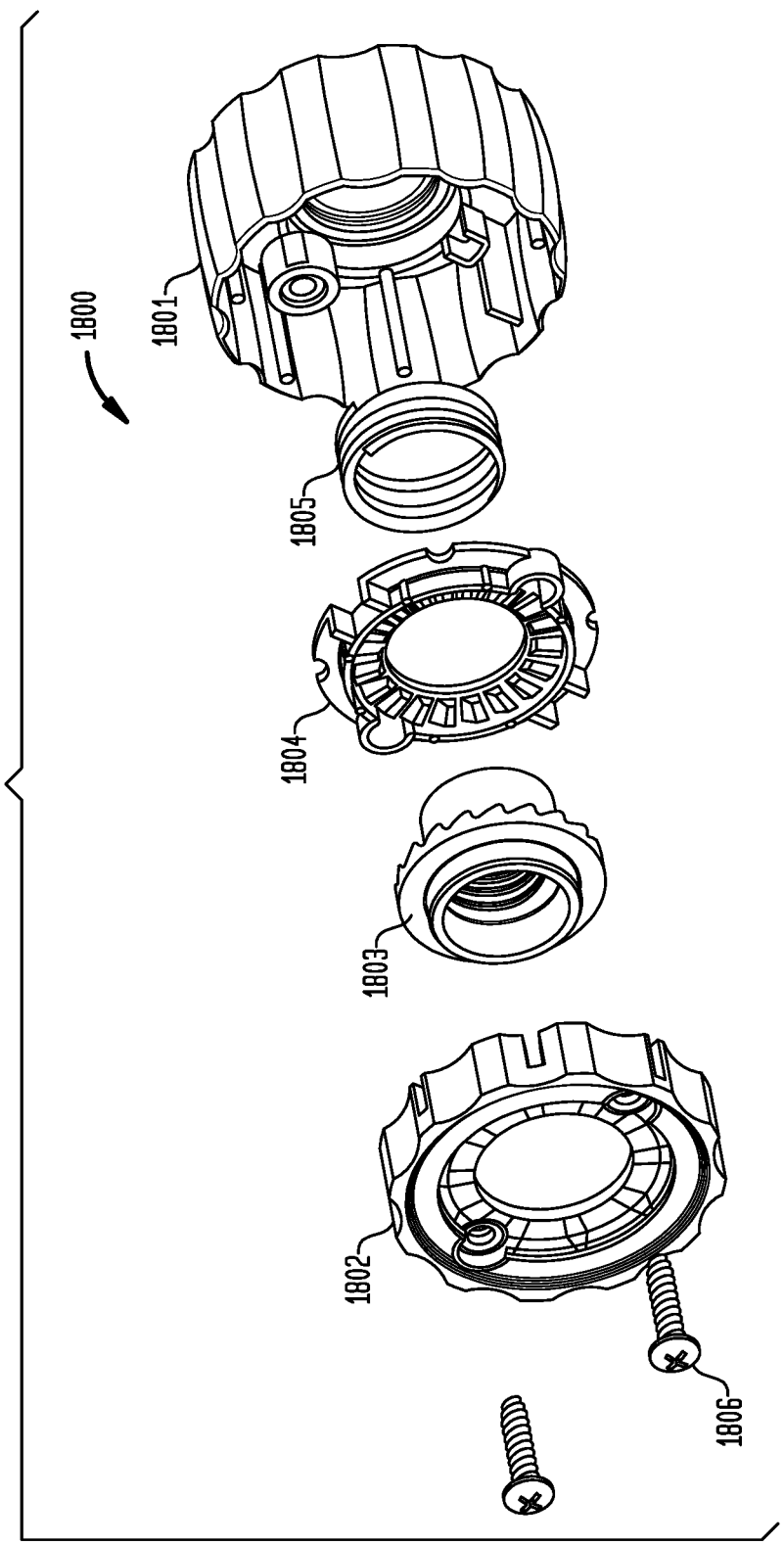

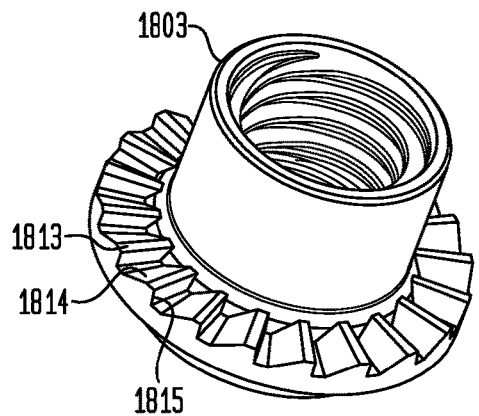
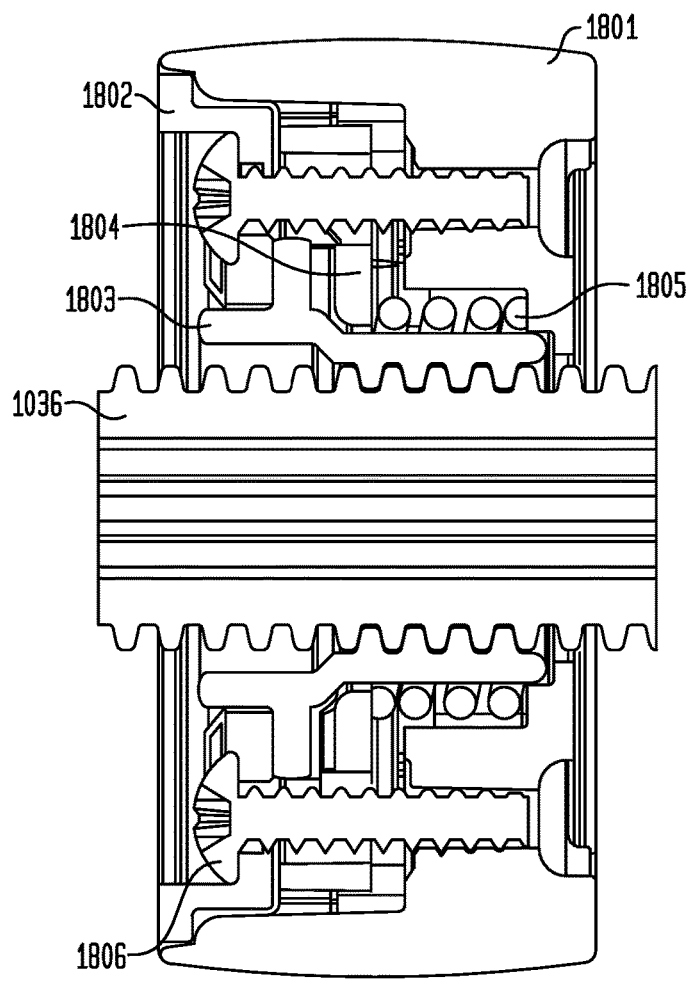
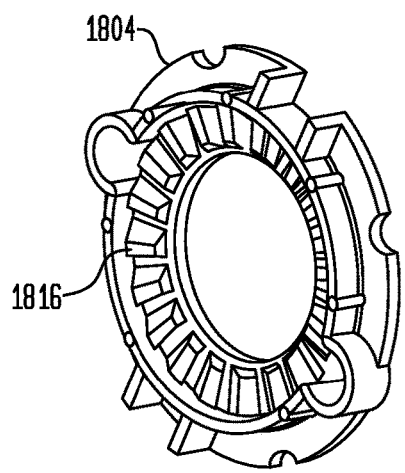

TRANSCATHETER DELIVERY SYSTEM WITH WHEEL ACTUATION

CROSS-REFERENCE TO RELATED APPLICATION

The present application is a Divisional Patent Applications of U.S. application Ser. No. 15/976,282 filed May 10, 2018, which claims the benefit of U.S. Provisional Patent Application No. 62/506,251 filed May 15, 2017, the disclosure of which is hereby incorporated herein by reference.

BACKGROUND OF THE INVENTION

The present disclosure relates to a delivery system for heart valve replacement and, in particular, for replacement of collapsible prosthetic heart valves. More particularly, the present disclosure relates to delivery systems for collapsible prosthetic heart valves that may be repositioned during the deployment procedure.

Prosthetic heart valves that are collapsible to a relatively small circumferential size can be delivered into a patient less invasively than valves that are not collapsible. For example, a collapsible valve may be delivered into a patient via a tube-like delivery apparatus such as a catheter, a trocar, a laparoscopic instrument, or the like. This collapsibility can avoid the need for a more invasive procedure such as full open-chest, open-heart surgery.

Collapsible prosthetic heart valves typically take the form of a valve structure mounted on a stent. There are two types of stents on which the valve structures are ordinarily mounted: a self-expanding stent and a balloon-expandable stent. To place such valves into a delivery apparatus and ultimately into a patient, the valve must first be collapsed or crimped to reduce its circumferential size.

When a collapsed prosthetic valve has reached the desired implant site in the patient (e.g., at or near the annulus of the patient's heart valve that is to be replaced by the prosthetic valve), the prosthetic valve can be deployed or released from the delivery apparatus and re-expanded to full operating size. For balloon-expandable valves, this generally involves releasing the entire valve, assuring its proper location, and then expanding a balloon positioned within the valve stent. For self-expanding valves, on the other hand, the stent automatically expands as the sheath covering the valve is withdrawn.

In conventional delivery systems for self-expanding aortic valves, for example, after the delivery system has been positioned for deployment, the annulus end of the valve is typically unsheathed and expanded first, while the aortic end of the valve remains sheathed. Once the annulus end of the valve has expanded, it may be determined that the valve needs to be repositioned in the patient's aortic annulus. To accomplish this, a user (such as a surgeon or an interventional cardiologist) typically resheathes the annulus end of the valve so that the valve can be repositioned while in a collapsed state. After the valve has been repositioned, the user can again release the valve.

Once a self-expanding valve has been fully deployed, it expands to a diameter larger than that of the sheath that previously retained the valve in the collapsed condition, making resheathing difficult. In order for the user to be able to more readily resheathe a valve, it is preferable that the valve be only partially deployed, with a portion of the valve still collapsed inside of the sheath.

Despite the various improvements that have been made to the collapsible prosthetic heart valve delivery process, conventional delivery devices, systems, and methods suffer from some shortcomings. For example, in some delivery devices for self-expanding valves, it is difficult to control how much of the valve remains in the sheath during a partial deployment, and the user may accidentally deploy the valve fully before verifying that the annulus end of the valve is in the optimal position in the patient's valve annulus, thereby taking away the opportunity to resheathe and reposition the valve. Moreover, it is difficult during prosthetic heart valve delivery to determine whether a valve assembly will function as intended without full deployment of the heart valve. Due to anatomical variations between patients, a fully deployed heart valve may need to be removed from the patient if it appears that the valve is not functioning properly. Removing a fully deployed heart valve increases the length of the procedure and increases the risk of infection and/or damage to heart tissue.

There therefore is a need for further improvements to the devices, systems, and methods for transcatheter delivery of collapsible prosthetic heart valves, and in particular, self-expanding prosthetic heart valves. Among other advantages, the present disclosure may address one or more of these needs.

SUMMARY OF THE INVENTION

In some embodiments, a delivery device for a collapsible prosthetic heart valve includes an inner shaft, a distal sheath disposed about a portion of the inner shaft and forming a compartment with the inner shaft, the compartment being adapted to receive the prosthetic heart valve, the inner shaft and the distal sheath being movable relative to one another, and a handle including a frame having a longitudinal axis, a proximal end and a distal end, the handle further including a deployment actuator and a hub, each of the deployment actuator and the hub being independently capable of opening and closing the compartment, the hub further including a hub actuator coupled to the inner shaft.

In some embodiments, a delivery device for a collapsible prosthetic heart valve includes an inner shaft, a distal sheath disposed about a portion of the inner shaft and forming a compartment with the inner shaft, the compartment being adapted to receive the prosthetic heart valve, the inner shaft and the distal sheath being movable relative to one another, and a handle including a frame having a longitudinal axis, a proximal end and a distal end, the handle further including a deployment actuator a resheathing lock having a lock body coupled to a protruding lock finger in contact with a compression spring, a lock arm coupled to the lock finger, and a lock cap coupled to the lock arm.

In some embodiments, a delivery device for a collapsible prosthetic heart valve includes an inner shaft, a distal sheath disposed about a portion of the inner shaft and forming a compartment with the inner shaft, the compartment being adapted to receive the prosthetic heart valve, the inner shaft and the distal sheath being movable relative to one another, and a handle including a frame having a longitudinal axis, a proximal end and a distal end, the handle further including a deployment actuator, the deployment actuator being coupled to a clutch mechanism that permits movement of the distal sheath in a first condition and impedes movement of the distal sheath in a second condition.

BRIEF DESCRIPTION OF THE DRAWINGS

Various embodiments of the present delivery system are disclosed herein with reference to the drawings, wherein:

FIG. 3A is side view of an operating handle for a transfemoral delivery device for a collapsible prosthetic heart valve, shown with a side elevational view of the distal portion of a transfemoral catheter assembly;

FIG. 10A is a schematic exploded view of an actuator having a clutch mechanism;

FIG. 10B is a longitudinal cross-sectional view of the actuator of FIG. 10A;

FIGS. 10C-D are perspective views of an exemplary drive nut and clutch plate of the actuator of FIG. 10A.

Various embodiments of the present disclosure will now be described with reference to the appended drawings. It is to be appreciated that these drawings depict only some embodiments of the disclosure and are therefore not to be considered limiting of its scope.

DETAILED DESCRIPTION

As used herein in connection with prosthetic heart valves, the term "proximal" refers to the end of the heart valve closest to the heart when the heart valve is implanted in a patient, whereas the term "distal" refers to the end of the heart valve farthest from the heart when the heart valve is implanted in a patient. When used in connection with devices for delivering a prosthetic heart valve into a patient, the terms "proximal" and "distal" are to be taken as relative to the user of the delivery devices. "Proximal" is to be understood as relatively close to the user, and "distal" is to be understood as relatively farther away from the user.

Figure 1:
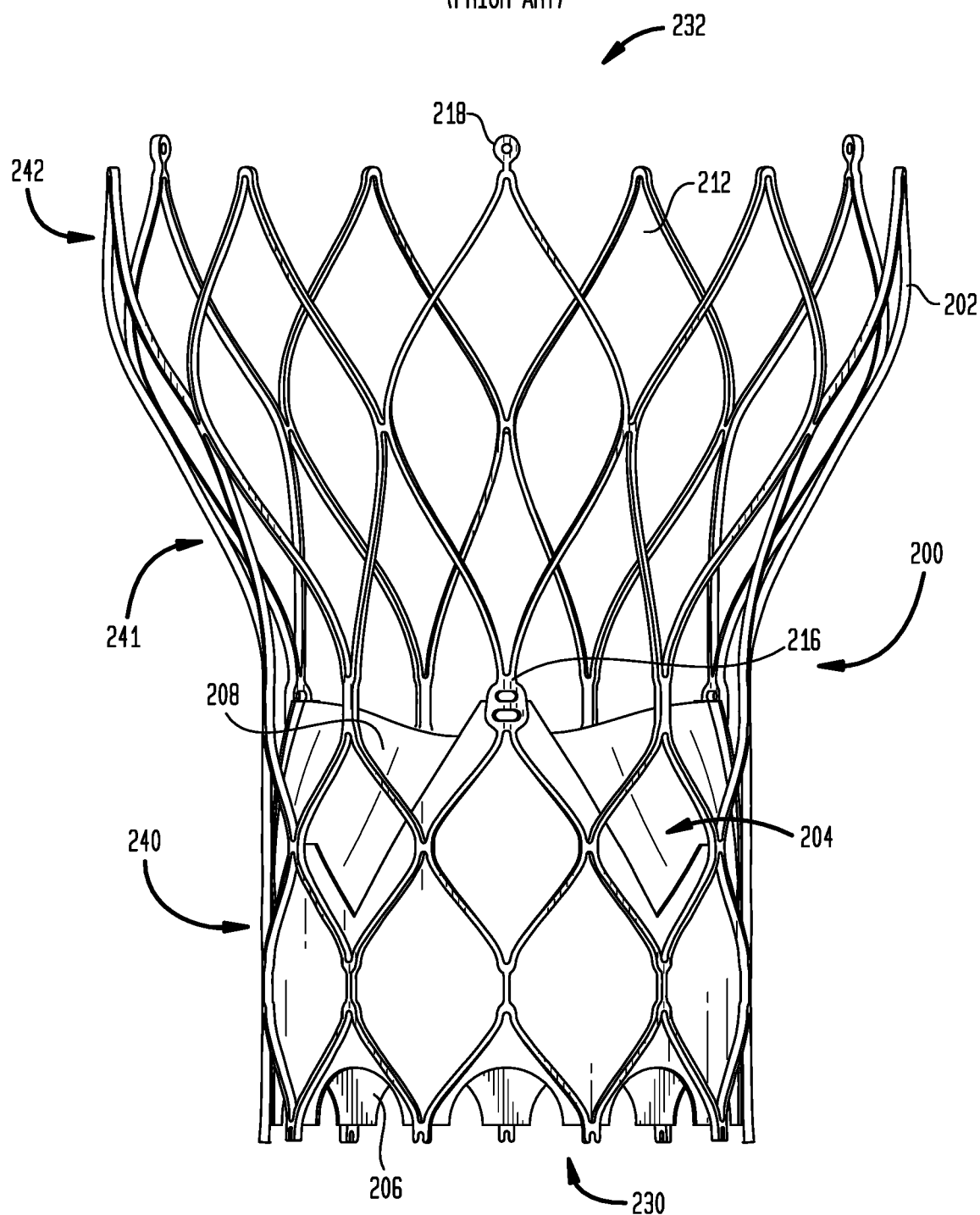
FIG. 1 is a side elevational view of a prior art collapsible prosthetic heart valve in an expanded condition, showing the valve assembly attached to the stent.

FIG. 1 shows a collapsible prosthetic heart valve 200 according to the prior art. The prosthetic heart valve 200 is designed to replace the function of a native aortic valve of a patient. Examples of collapsible prosthetic heart valves are described in International Patent Application Publication No. WO/2009/042196; and U.S. Pat. Nos. 7,018,406 and 7,329,278, the disclosures of all of which are hereby incorporated herein by reference. As discussed in detail below, the prosthetic heart valve has an expanded condition, shown in FIG. 1, and a collapsed condition. Although the delivery system is described herein in connection with its use to deliver a prosthetic heart valve for replacing a native aortic valve, the delivery system is not so limited, and may be used to deliver prosthetic valves for replacing other types of native or prosthetic cardiac valves.

Prosthetic heart valve 200 includes an expandable stent 202 which may be formed from any biocompatible material, such as metals, synthetic polymers or biopolymers capable of functioning as a stent. Stent 202 extends from a proximal or annulus end 230 to a distal or aortic end 232, and includes an annulus section 240 adjacent the proximal end and an aortic section 242 adjacent the distal end. The annulus section 240 has a relatively small cross-section in the expanded condition, while the aortic section 242 has a relatively large cross-section in the expanded condition. Preferably, annulus section 240 is in the form of a cylinder having a substantially constant diameter along its length. A transition section 241 may taper outwardly from the annulus section 240 to the aortic section 242. Each of the sections of the stent 202 includes a plurality of cells 212 connected to one another in one or more annular rows around the stent. For example, as shown in FIG. 1, the annulus section 240 may have two annular rows of complete cells 212 and the aortic section 242 and transition section 241 may each have one or more annular rows of partial cells 212. The cells 212 in the aortic section 242 may be larger than the cells 212 in the annulus section 240. The larger cells in the aortic section 242 better enable the prosthetic valve 200 to be positioned without the stent structure interfering with blood flow to the coronary arteries.

Stent 202 may include one or more retaining elements 218 at the distal end 232 thereof, the retaining elements being sized and shaped to cooperate with female retaining structures provided on the deployment device. The engagement of retaining elements 218 with the female retaining structures on the deployment device helps maintain prosthetic heart valve 200 in assembled relationship with the deployment device, minimizes longitudinal movement of the prosthetic heart valve relative to the deployment device during unsheathing or resheathing procedures, and helps prevent rotation of the prosthetic heart valve relative to the deployment device as the deployment device is advanced to the target location and during deployment.

The prosthetic heart valve 200 includes a valve assembly 204 positioned in the annulus section 240. Valve assembly 204 includes a cuff 206 and a plurality of leaflets 208 which collectively function as a one-way valve. The commissure between adjacent leaflets 208 may be connected to commissure features 216 on stent 202. FIG. 1 illustrates a prosthetic heart valve for replacing a native tricuspid valve, such as the aortic valve. Accordingly, prosthetic heart valve 200 is shown in FIG. 1 with three leaflets 208, as well as three commissure features 216. As can be seen in FIG. 1, the commissure features 216 may lie at the intersection of four cells 212, two of the cells being adjacent one another in the same annular row, and the other two cells being in different annular rows and lying in end-to-end relationship. Preferably, commissure features 216 are positioned entirely within annulus section 240 or at the juncture of annulus section 240 and transition section 241. Commissure features 216 may include one or more eyelets which facilitate the suturing of the leaflet commissure to the stent. However, it will be appreciated that the prosthetic heart valves may have a greater or lesser number of leaflets and commissure features. Additionally, although cuff 206 is shown in FIG. 1 as being disposed on the luminal surface of annulus section 240, it is contemplated that the cuff may be disposed on the abluminal surface of annulus section 240, or may cover all or part of either or both of the luminal and abluminal surfaces of annulus section 240. Both the cuff 206 and the leaflets 208 may be wholly or partly formed of any suitable biological material or polymer.

In operation, a prosthetic heart valve, including the prosthetic heart valve described above, may be used to replace a native heart valve, such as the aortic valve, a surgical heart valve or a heart valve that has undergone a surgical procedure. The prosthetic heart valve may be delivered to the desired site (e.g., near a native aortic annulus) using any suitable delivery device, including the delivery devices described in detail below. During delivery, the prosthetic heart valve is disposed inside the delivery device in the collapsed condition. The delivery device may be introduced into a patient using a transfemoral, transapical or transseptal approach. Once the delivery device has reached the target site, the user may deploy the prosthetic heart valve. Upon deployment, the prosthetic heart valve expands into secure engagement within the native aortic annulus. When the prosthetic heart valve is properly positioned inside the heart, it works as a one-way valve, allowing blood to flow in one direction and preventing blood from flowing in the opposite direction.

In a prosthetic heart valve, the valve assembly may be spaced from the distal or aortic end of the stent by a distance that enables deployment of the heart valve by an amount sufficient for the valve leaflets of the prosthetic valve to operate as intended, while the distal end of the stent remains captured by the delivery device. More particularly, as will be explained further below, the annulus end of the prosthetic heart valve may be deployed first, while the aortic end of the prosthetic heart valve remains at least partially covered by a distal sheath of the delivery device. The annulus portion of the prosthetic heart valve may be deployed so that the entirety of the valve leaflets, up to and including the commissures, is deployed and fully operational. By deploying the prosthetic heart valve in this manner, the user can determine whether the valve leaflets are properly positioned relative to the native valve annulus, and whether the valve is functioning properly. If the user determines that the positioning and operation of the valve are acceptable, the remainder of the valve may be deployed. However, if it is determined that the leaflet position is improper or that the valve is not functioning properly, the user may resheathe the valve and either reposition it for redeployment, or remove it entirely from the patient. This can be particularly important in very high risk patients who would typically be recipients of these types of valves because of the nature of their condition and the impact that may have on the shape and/or condition of the native valve and valve annulus.

As is shown in FIG. 1, in one embodiment the entirety of valve assembly 204, including the leaflet commissures, is positioned in the annulus section 240 of stent 202. When opened, the leaflets may extend further into the transition section 241 or may be designed such that they remain substantially completely within the annulus section. That is, substantially the entirety of valve assembly 204 is positioned between the proximal end 230 of stent 202 and the commissure features 216, and none of the valve assembly 204 is positioned between commissure features 216 and the distal end 232 of the stent. Indeed, in some embodiments, the valve can be designed such that, upon partial deployment, the commissure features are fully exposed, oriented generally parallel to the direction of blood flow, and at or near their actual radially expanded positions (but not necessarily their eventual positions relative to the annulus), such that the leaflets can operate substantially as they would when the valve is fully deployed, even though enough of the stent is still retained within the delivery device or sheath to permit resheathing.

In a preferred arrangement, the distance between commissure features 216 and the distal end 232 of stent 202 will be about two-thirds of the length of the stent from the proximal end 230 to the distal end. This structural arrangement provides advantages in the deployment of prosthetic valve 200 as will be discussed in more detail with reference to FIGS. 2A and 2B. By having the entirety of valve assembly 204 positioned within annulus section 240, and by having a sufficient distance between commissure features 216 and the distal end 232 of stent 202, the valve assembly and commissures will not impede blood flow into the coronary arteries and will not interfere with access thereto during cardiac intervention, such as angiography, annuloplasty or stent placement.

Further, it is possible to partially deploy prosthetic valve 200 so that the valve assembly 204 thereof is able to fully function in its intended position in the native valve annulus, while a sufficient amount of the aortic section 242 is retained within the delivery device should resheathing become necessary. In other words, as will be explained in more detail below, the user may withdraw the distal sheath of the delivery device to gradually expose prosthetic valve 200, beginning at the proximal end 230. Continued withdrawal of the distal sheath will expose a greater extent of the prosthetic valve until the entire annulus section 240 and valve assembly 204 have been exposed. Upon exposure, these portions of the prosthetic valve will expand into engagement with the native valve annulus, entrapping the native valves, except for a small portion immediately adjacent the free end of the distal sheath which will be constrained by the distal sheath from fully expanding.

However, once the distal sheath has been withdrawn to expose a sufficient portion of the aortic section 242, the annulus section 240 will be able to fully expand and valve assembly 204 will be able to function in the same manner as if the entirety of prosthetic valve 200 had been deployed. At this juncture, it will be possible for the user to ascertain whether annulus section 240 and valve assembly 204 have been properly positioned relative to the native valve annulus, and whether the valve assembly is functioning properly.

If the position and operation of valve assembly 204 are acceptable, the distal sheath may be withdrawn further to deploy the remainder of prosthetic valve 200. On the other hand, if the positioning or operation of valve assembly 204 are unacceptable, the user may advance the distal sheath to resheathe the prosthetic valve, reposition the valve and initiate the deployment procedure anew. And if it is determined that the valve is not functioning properly, it can be withdrawn from the patient and a new valve introduced.

Figure 2A:
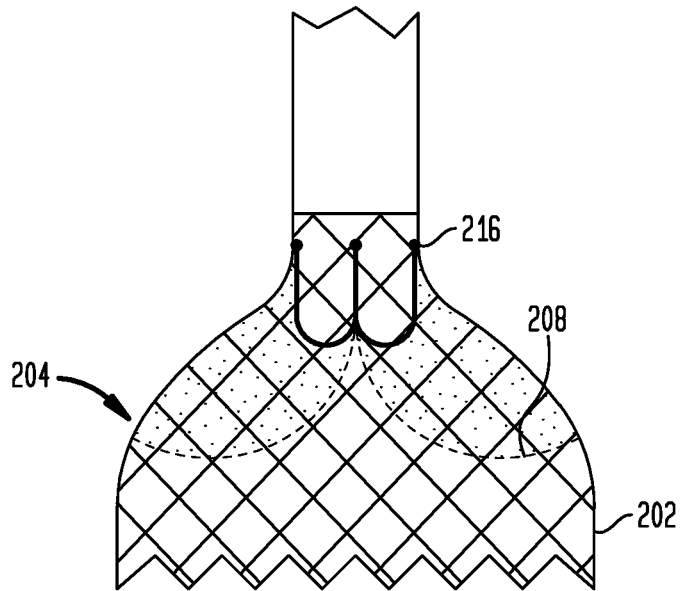
FIG. 2A is a highly schematic side elevational view showing partial deployment of a collapsible prosthetic heart valve with high placement according to the prior art.
Figure 2B:
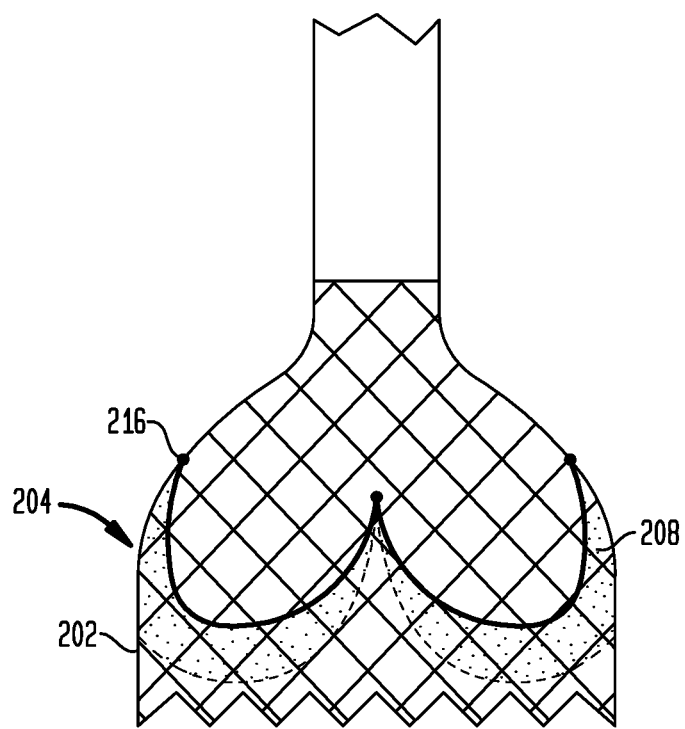
FIG. 2B is a highly schematic side elevational view showing partial deployment of a collapsible prosthetic heart valve with low placement according to the prior art.

It will be appreciated from the foregoing that the placement of the leaflets 208 within the stent 202 can affect the valve functioning during partial deployment. FIG. 2A illustrates a valve assembly 204 with high placement, while FIG. 2B illustrates a valve assembly with low placement. As used herein, the phrase "high placement" of a valve assembly refers to locating the valve assembly within the transition section 241 of the stent 202, or within the portion of the annulus section 240 closest to the transition section. The phrase "low placement" of a valve assembly refers to locating the valve assembly closer to the proximal end 230 of the stent 202 and entirely within the annulus section 240 thereof, such that the leaflets 208 are substantially disposed within the annulus section.

As seen in FIG. 2A, during partial deployment the annulus end of the heart valve 200 is unsheathed and allowed to expand. The distal end 232, including the aortic section 242, remains partially sheathed and coupled to the delivery device. Operation of the delivery device is described below in more detail with reference to FIGS. 3A-7B. Turning back to FIG. 2A, it will be appreciated that high placement of valve assembly 204 will cause the valve assembly to not be fully deployed when heart valve 200 is only partially deployed, thereby affecting leaflet function. Specifically, since the commissure features 216 are located closer to or within the transition section 241, they do not reach their fully expanded positions. As such, the leaflets 208 remain partially closed at this stage of deployment. Because of the location of the commissure features 216 and the leaflets 208, the valve assembly 204 cannot be tested during partial deployment. Instead, the user must unsheathe a portion of the aortic section 242 as well, which may pose problems if the valve assembly 204 is to be resheathed and redeployed.

In contrast to the prosthetic heart valve of FIG. 2A, the heart valve 200 of FIG. 2B exhibits low placement of the valve assembly 204 within the annulus section 240. Low placement of the valve assembly 204 enables the valve assembly to fully deploy when heart valve 200 is only partially deployed. As such, leaflets 208 reach their fully expanded and open positions during partial deployment and are able to function near normally, enabling a better assessment of the valve's functioning and final placement within the actual anatomy. Thus, if it appears that the valve needs to be moved, the heart valve 200 may be easily resheathed and repositioned. This concept is beneficial when dealing with less than ideal anatomical configurations.

The shape of the stent 202 during partial deployment will also affect the valve 204. If the stent shape is such that, while still partially retained by the sheath, it cannot open sufficiently to allow operation of the valve, it may not be possible to fully assess the operation of the valve in its intended placement position. Moreover, the height of the valve commissure features 216 relative to the proximal end 230 of the valve will affect the valve function. The lower the commissure features 216, meaning the closer to the proximal end 230, the more they will expand outwardly and the valve leaflets will be able to open during partial deployment, creating a flow passageway through the leaflets which approaches that of a fully deployed valve.

A transfemoral or transapical delivery device may be used to partially deploy the prosthetic heart valve such that an assessment may be made regarding flow through the valve and adequacy of coaptation. If, after the annulus section is unsheathed and the valve is tested, it is found that the valve needs to be repositioned, the annulus section may be resheathed and the valve redeployed as necessary.

Turning now to FIGS. 3A-D, an exemplary transfemoral delivery device 1010 for a collapsible prosthetic heart valve (or other types of self-expanding collapsible stents) has a catheter assembly 1016 for delivering the heart valve to and deploying the heart valve at a target location, and an operating handle 1020 for controlling deployment of the valve from the catheter assembly. The delivery device 1010 extends from a proximal end 1012 to a distal tip 1014. The catheter assembly 1016 is adapted to receive a collapsible prosthetic heart valve (not shown) in a compartment 1023 defined around an inner shaft 1026 and covered by a distal sheath 1024. The inner shaft 1026 extends through the operating handle 1020 to the distal tip 1014 of the delivery device, and includes a retainer 1025 affixed thereto at a spaced distance from distal tip 1014 and adapted to hold a collapsible prosthetic valve in the compartment 1023.

The distal sheath 1024 surrounds the inner shaft 1026 and is slidable relative to the inner shaft such that it can selectively cover or uncover the compartment 1023. The distal sheath 1024 is affixed at its proximal end to an outer shaft 1022, the proximal end of which is connected to the operating handle 1020 in a manner to be described. The distal end 1027 of the distal sheath 1024 abuts the distal tip 1014 when the distal sheath fully covers the compartment 1023, and is spaced apart from the distal tip 1014 when the compartment 1023 is at least partially uncovered.

The operating handle 1020 is adapted to control deployment of a prosthetic valve located in the compartment 1023 by permitting a user to selectively slide the outer shaft 1022 proximally or distally relative to the inner shaft 1026, or to slide the inner shaft 1026 relative to the outer shaft 1022, thereby respectively uncovering or covering the compartment with the distal sheath 1024. Operating handle 1020 includes frame 1030 which extends from a proximal end 1031 to a distal end and includes a top frame portion 1030*a* and a bottom frame portion 1030*b*. The proximal end of the inner shaft 1026 is coupled to a hub 1100, and the proximal end of the outer shaft 1022 is affixed to a carriage assembly 1040 (FIG. 4) that is slidable within the operating handle along a longitudinal axis of the frame 1030, such that a user can selectively slide the outer shaft relative to the inner shaft by sliding the carriage assembly relative to the frame. Alternatively, inner shaft 1026 may be actuated via hub 1100 to cover or uncover the compartment as will be discussed in greater detail below. Optionally, a stability sheath 1051 is disposed over some or all of outer shaft 1022. The stability sheath 1051 may be attached to the outer shaft 1022 or may be unattached. Additionally, stability sheath 1051 may be disposed over a majority of outer shaft 1022 or over a minority of the outer shaft (e.g., over 49% or less, over 33%, etc.). Optionally, stability sheath 1051 may be more rigid than outer shaft 1022.

Figure 3B:
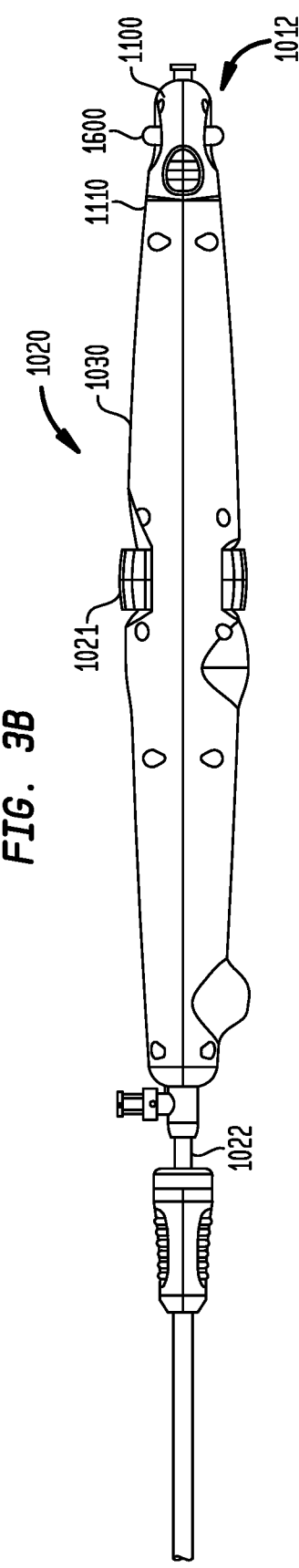
FIGS. 3B-D are side and top views of the operating handle of FIG. 3A, and an enlarged side view of the hub in the proximal-most position, respectively.
Figure 3C:
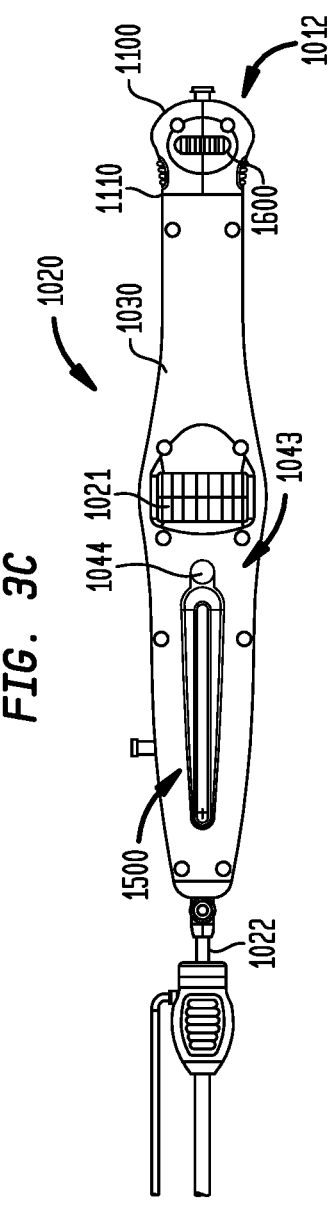
Figure 3D:
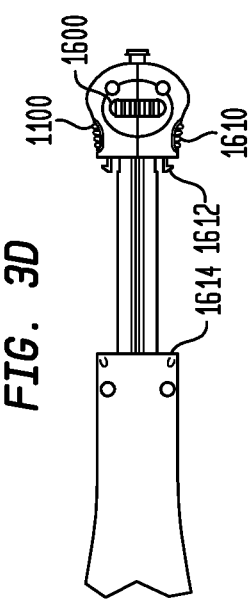
Figure 4:
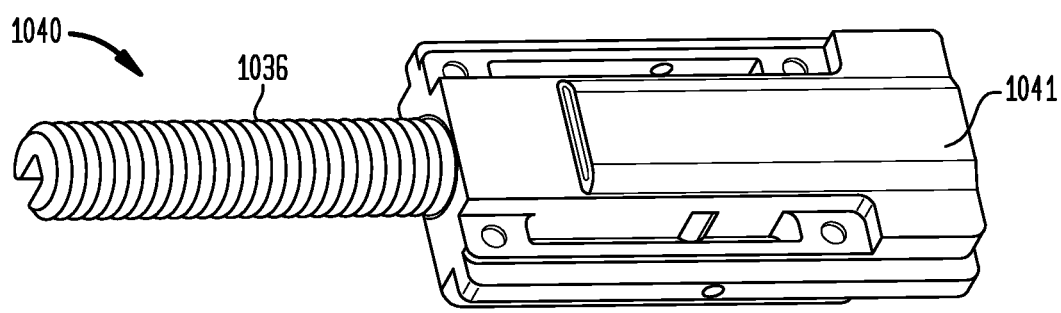
FIG. 4 is an enlarged perspective view of the carriage assembly of the handle of FIG. 3A.

Additionally, hub 1100 may include a pair of buttons 1610, each attached to a clip 1612 (FIG. 3D). Clips 1612 on hub 1100 may mate with voids 1614 on frame 1030 to ensure that the hub and the frame are securely coupled together. Optionally, hub 1100 may also include a wheel 1600, which will be described in greater detail below.

Figure 5:
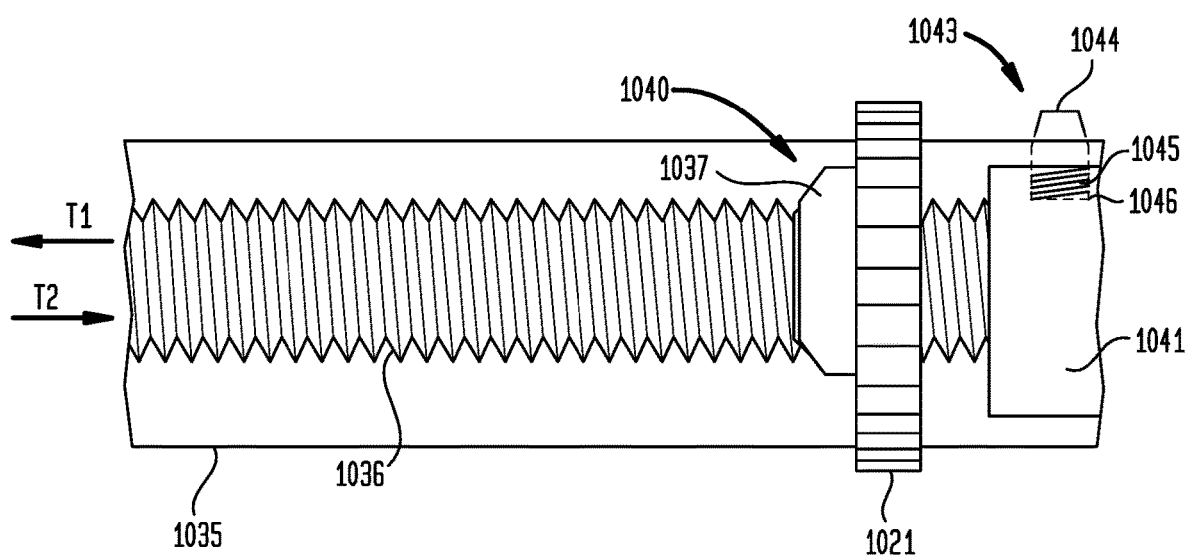
FIG. 5 is an enlarged schematic representation of a portion of the threaded rod of the carriage assembly of the operating handle.
Figure 6:
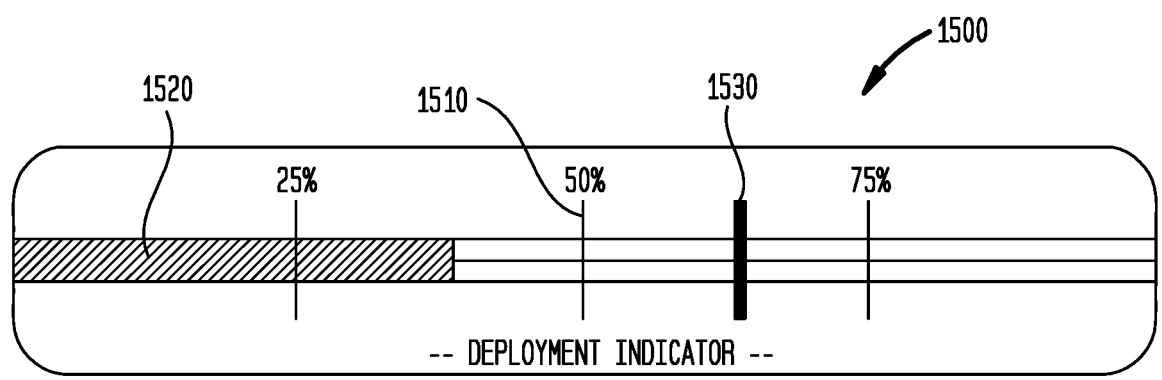
FIG. 6 shows a deployment indicator for use with the operating handle.

A first mechanism for covering and uncovering the compartment 1023 will be referred to as a "fine" technique as covering and uncovering occurs slowly with a high degree of precision. To allow for this technique, frame 1030 defines an elongated space 1035 in which carriage assembly 1040 may travel (FIG. 5). The elongated space preferably permits the carriage assembly 1040 to travel a distance that is at least as long as the anticipated length of the prosthetic valve to be delivered (e.g., at least about 50 mm), such that the distal sheath 1024 can be fully retracted off of the prosthetic valve.

The carriage assembly 1040 includes a main body 1041 and a threaded rod 1036 extending proximally therefrom along the longitudinal axis of the frame 1030. The threaded rod 1036 preferably is longer than the anticipated maximum travel distance of the carriage assembly 1040 within the elongated space 1035 (e.g., at least about 50 mm), such that the threaded rod does not fully withdraw from the elongated space 1035 during deployment of the prosthetic valve.

A deployment actuator 1021, shown in FIGS. 3A-D as a wheel protruding from the upper and lower frames 1030a, 1030b is fixedly coupled to a first gear 1037 so that rotation of actuator 1021 causes a corresponding rotation of gear 1037. Gear 1037, in turn, is threadedly engaged on the threaded rod 1036. Gear 1037 converts rotation of deployment actuator 1021 into longitudinal translation of threaded rod 1036 in the direction of arrows T1 and T2 and a corresponding translation of main body 1041. Hence, rotation of actuator 1021 in one direction (either clockwise or counterclockwise depending on the orientation of the threads on the threaded rod 1036) causes the carriage assembly 1040 to translate proximally in direction T1 within the elongated space 1035. Alternatively, actuator 1021 and first gear 1037 may be integral with one another.

Figure 7A:
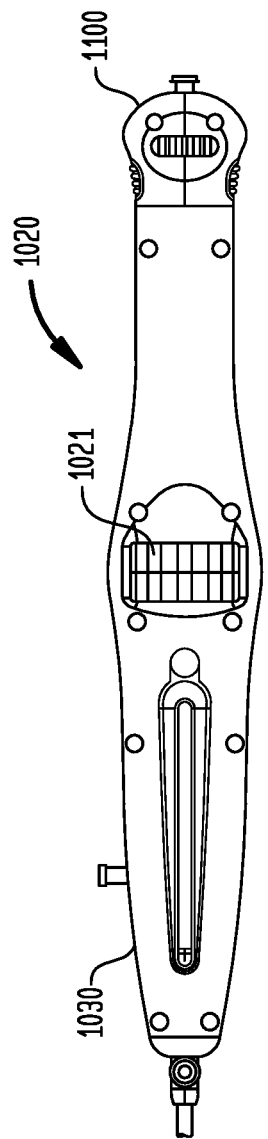
FIGS. 7A-B are schematic illustrations showing the use of the operating handle of FIG. 3A.
Figure 7B:
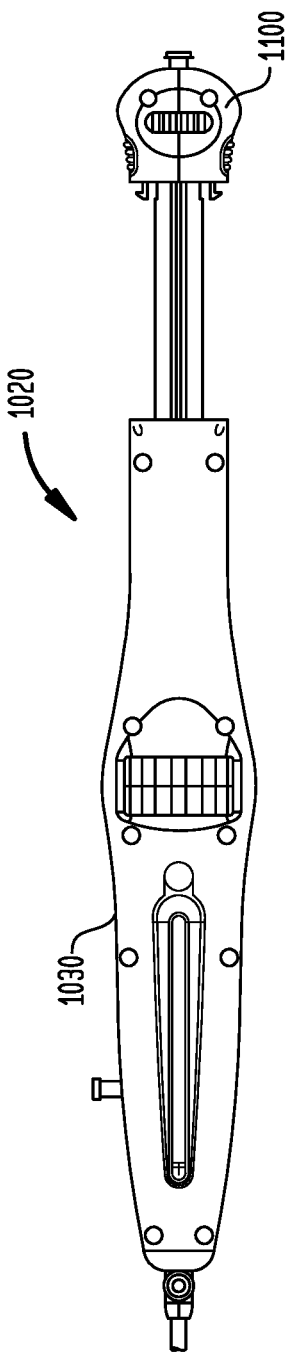

As outer shaft 1022 is fixedly connected to carriage assembly 1040, translation of the carriage assembly results in a longitudinal translation of outer shaft 1022 and with it distal sheath 1024. Thus, deployment actuator 1021 is configured to provide for fine movement of outer shaft 1022 for deployment and recapture of the prosthetic heart valve. As deployment actuator 1021 protrudes from upper and lower frames 1030a,1030b approximately halfway between the proximal and distal ends of the handle 1020, a user may readily rotate the actuator with his or her thumb and/or index finger (FIG. 7A).

Optionally, handle 1020 further includes a resheathing lock 1043 adapted to prevent any movement of the carriage assembly within the frame 1030, thereby preventing a user from accidentally initiating deployment of a prosthetic valve (FIG. 3C). Resheathing lock 1043 may be coupled to the main body 1041 of carriage assembly 1040. The resheathing lock 1043 may include a laterally projecting pin 1044 that is slidable within a hole 1046 in main body 1041. Pin 1044 may have a first or unlocked condition in which it is compressed between main body 1041 and frame 1030.

As the user rotates deployment actuator 1021, outer shaft 1022 is pulled back and with it distal sheath 1024 to uncover a portion of compartment 1023. This process may continue until a predetermined position just prior to a position at which resheathing is no longer possible. When this predetermined position is reached, a spring 1045 positioned in hole 1046 between main body 1041 and pin 1044 pushes the pin out through an aperture in frame 1030 to a second or locked condition (FIG. 5) in which the pin protrudes from frame 1030, providing a visual indicator to the user that resheathing is no longer possible past this predetermined position. Further translation of the carriage assembly 1040 may be impeded until the user presses pin 1044 to the interior of frame 1030 against the action of spring 1045 to confirm that further uncovering of compartment 1023 is desired (i.e., that the user wishes to fully deploy the prosthetic heart valve in its current position).

The initial distance that the carriage assembly 1040 can travel before actuating resheathing lock 1043 may depend on the structure and size of the particular prosthetic valve to be deployed. Preferably, the initial travel distance of the carriage assembly 1040 is about 3 mm to about 5 mm less than the length of the valve in the collapsed condition (e.g., about 3 mm to about 5 mm of the valve may remain covered to permit resheathing). Alternatively, the initial travel distance of the carriage assembly 1040 may be about 40 mm to about 45 mm, which is about 80% to about 90% of the length of an exemplary 50 mm valve. In other arrangements, the initial distance that the carriage assembly 1040 can travel can be determined as a percentage of the length of the prosthetic valve in the collapsed condition and/or of the compartment 1023, including, for example, 50%, 60%, 70%, 75%, 85%, 95% or anywhere between about 50% and about 95%. Thus, resheathing lock 1043 may allow uncovering of compartment 1023 up to a maximum distance or percentage, and allow further uncovering only after the user has pressed on laterally projecting pin 1044 to confirm that additional release (e.g., full release of the prosthetic heart valve) is desired.

A second technique, referred to as a "coarse technique," may be used to cover and uncover compartment 1023 more quickly and with less precision than the fine technique described above. Specifically, hub 1100 may be coupled to the proximal end of inner shaft 1026 and may be capable of moving the inner shaft relative to frame 1030 to facilitate opening and closing of the compartment 1023. This coarse movement may be used when no prosthetic heart valve is present in the compartment, such as, for example, when the compartment is to be opened prior to loading the prosthetic heart valve, and when the compartment is to be closed after the valve has been fully deployed. A mechanical lock 1110 may couple hub 1100 to frame 1030 to prevent accidental movement during use of operating handle 1020. For example, hub 1100 and a portion of frame 1030 may be threadedly engaged such that a rotation of the hub relative to the frame is required to release the hub from the frame. Other types of mechanical locks that will releasably couple hub 1100 to frame 1030 as intended will be known to those skilled in the art. After lock 1110 has been disengaged, hub 1100 may be used to quickly cover or uncover compartment 1023. Movement of inner shaft 1026 with respect to outer shaft 1022 may open and close the compartment. Thus, pushing hub 1100 distally (and thus the distal movement of inner shaft 1022) opens compartment 1023 and pulling hub 1100 proximally closes the compartment.

Optionally, an indicator window 1500 (FIG. 6) may be disposed on top of frame 1030 and may include a series of increments 1510 showing a percent or extent of deployment of the prosthetic heart valve. A scrolling bar 1520 may move along window 1500 past the series of increments 1510 as deployment continues to illustrate to the user the extent to which the prosthetic heart valve has been deployed. As illustrated, scrolling bar 1520 indicates that a prosthetic heart valve is approximately 37.5% deployed. Indicator window 1500 further includes a critical indicator 1530 showing the position past which resheathing is no longer possible. Resheathing lock 1043 may be activated as scrolling bar 1520, which is coupled to the main body 1041 of carriage assembly 1040 reaches position 1530.

The general operation of the delivery device 1010 to deploy a prosthetic valve will now be described. Device 1010 may be shipped with outer shaft 1022 in its proximal-most position. Hub 1100 may also be initially shipped in a proximal-most position, the hub being spaced away from frame 1030. (FIG. 7B) However, compartment 1023 will be covered by distal sheath 1024. To load the delivery device 1010 with a collapsible prosthetic valve, a user can push hub 1100 distally (and advance inner shaft 1026) to expose the compartment 1023 (FIG. 7A), thread the inner shaft 1026 through the valve, collapse the valve and couple it to a retainer, and rotate deployment actuator 1021 to advance the distal sheath back over compartment 1023 to fully cover the valve. In this starting condition, the handle 1020 will be in an initial state with the carriage assembly 1040 at its distalmost position within the frame 1030, the resheathing lock 1043 will be in an unlocked state with pin 1044 disposed within frame 1030, the hub 1100 will be in its distal-most position and coupled to frame 1030, and the deployment indicator will show 0% deployment.

To use the operating handle 1020 to deploy the prosthetic valve, the user can rotate the deployment actuator 1021, causing the carriage assembly 1040 to slide proximally within the elongated space 1035 in frame 1030. Because the distal sheath 1024 is affixed to the outer shaft 1026, which in turn is affixed to the carriage assembly 1040, sliding the carriage assembly proximally relative to the frame will cause the distal sheath to move proximally. Since the inner shaft 1026 is at this point fixed to frame 1030, it will not move. Hence, the proximal movement of distal sheath 1024 relative to inner shaft 1022 will uncover the compartment 1023, thereby exposing and initiating deployment of the valve located therein.

Movement of the carriage assembly 1040 proximally may continue only until the resheathing lock 1043 is actuated and pin 1044 protrudes from frame 1030. At this point, the distal sheath 1024 will not be fully withdrawn from around the compartment 1023, and the prosthetic valve will not be fully deployed. Moreover, indicator window 1500 will show that scrolling bar 1520 has reached critical indicator 1530 and that any further uncovering of the compartment will fully deploy the prosthetic heart valve and prevent its resheathing.

When the deployment procedure has reached this juncture, the user can evaluate the position of the valve and determine whether the annulus end of the valve is properly aligned relative to the patient's native valve annulus. If repositioning is desired, the user may resheathe the valve by using deployment actuator 1021 to slide the carriage assembly 1040 distally within the frame 1030, thereby moving the distal sheath 1024 distally over the compartment 1023 and over the partially deployed valve to recollapse the expanded portion of the valve. With the valve resheathed, the user can reposition the catheter assembly 1016 and commence the deployment procedure once again.

Once the valve has been properly positioned relative to the aortic annulus, the user may complete the deployment process. To do so, the user presses pin 1044 through the aperture in frame 1030, releasing lock 1043, which frees carriage assembly 1040 to continue its movement proximally within the frame. The user can complete the deployment of the valve by continuing to slide the carriage assembly 1040 proximally, for example, by rotating the deployment actuator 1021. When the valve has been fully unsheathed, the stent portion of the valve self-expands and disengages from the retainer 1025, thereby releasing the valve from the catheter assembly 1016, following valve deployment, hub 1100 may once again be used to quickly cover the compartment and the delivery device may be removed from the patient.

Three additional features may be added to the delivery device 1010 described above to improve the performance of the device. It will be understood that all three of these features are optional, and that the delivery device may include none of the features, one of the features, or a combination of the features as desired. The three features are the optional use of a second wheel for gap closure, a robust resheathing lock mechanism, and an actuator clutch mechanism. Each will be described, in turn, with reference to FIGS. 8-10.

Figure 8A:
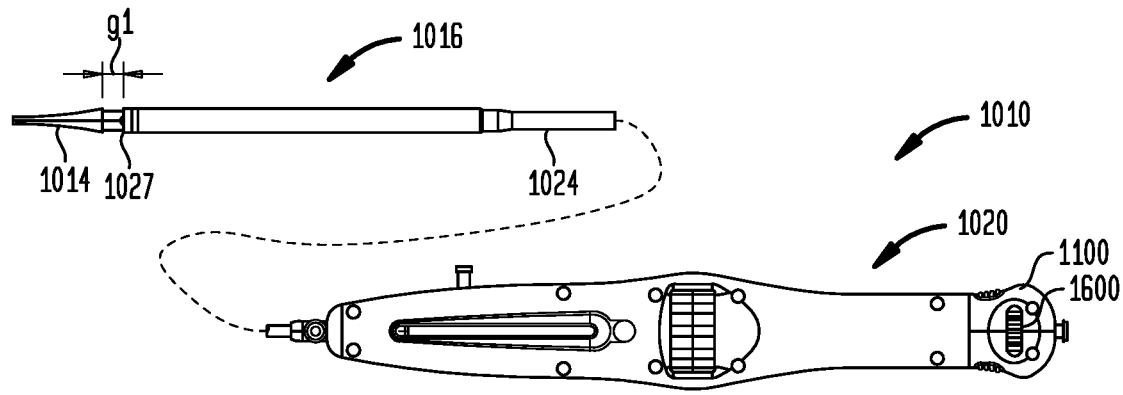
FIG. 8A is a schematic illustration showing the use of a second wheel to close a gap between a distal sheath and a distal tip of a delivery device.
Figure 8B:
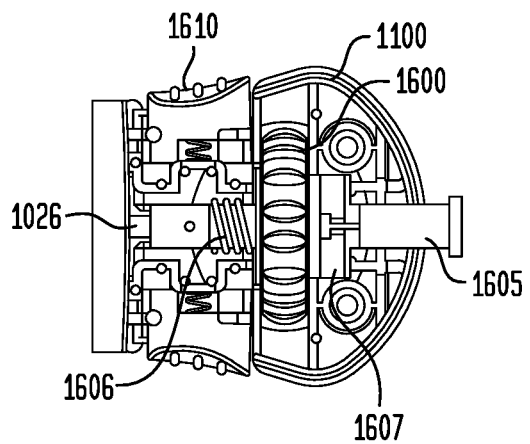
FIGS. 8B-C are longitudinal cross-sectional views of the proximal end of the operating handle of FIG. 3A showing the use of the second wheel to close the gap between the distal sheath and the distal tip of the delivery device.
Figure 8C:
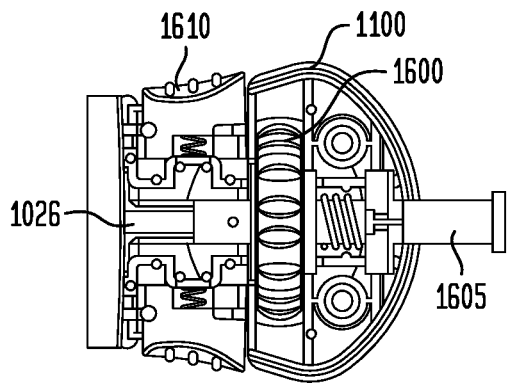

FIGS. 8A-C illustrate the use of additional features on the hub 1100 to aid in valve loading and delivery. As discussed, the delivery device 1010 may be packaged with the hub 1100 withdrawn to the proximal position and the deployment actuator 1021 turned such that the distal sheath 1024 is in its proximal position, leaving a closed capsule (see FIG. 3A). Hub 1100 may be moved distally to move inner shaft 1026 to its distal position and thus open the compartment 1023 for valve loading. After the valve has been loaded, actuator 1021 may be rotated to move the distal sheath 1024 over the valve and close the compartment 1023. The delivery device 1010 is designed such that the distal end 1027 of the distal sheath 1024 abuts the distal tip 1014 when the distal sheath fully covers the compartment 1023, and is spaced apart from the distal tip 1014 when the compartment 1023 is at least partially uncovered.

As shown in FIG. 8A, in some circumstances, though the actuator 1021 has been properly used to close the compartment 1023, the distal end 1027 of the distal sheath 1024 may not abut the distal tip 1014, leaving a gap g1 between the distal end of the sheath and the distal tip 1014. This gap may be due to residual compression in distal sheath 1024 and/or frictional forces between distal sheath 1024 and the loaded prosthetic heart valve. In effect, though distal sheath 1024 has been fully moved to its distal-most position with respect to the shaft 1026, it may be slightly bunched together and not fully extended, leaving gap g1.

To close the gap g1, a second wheel 1600 may be used, the details of which are shown in FIGS. 8B-C. Wheel 1600 may be disposed in hub 1100 and mounted over cam 1605 having threaded portion 1606, cam 1605 in turn being coupled to inner shaft 1026. Turning wheel 1600 while holding frame 1030 may pull cam 1605, and thus inner shaft 1026, proximally to close the gap g1 and force the distal end 1027 of distal sheath 1024 to abut distal tip 1014 (FIG. 8C). Once the gap g1 is closed, wheel 1600 may be rotated in the opposite direction to relieve any tension within the distal sheath 1024 (FIG. 8B). A flange 1607 on cam 1605 may contact wheel 1600 and create a hard stop position when returning inner shaft 1026 to a neutral position. In some embodiments, wheel 1600 allows for translation of shaft 1026 by between about 0.25 inch and about 1 inch relative to distal sheath 1024.

Figure 9A:
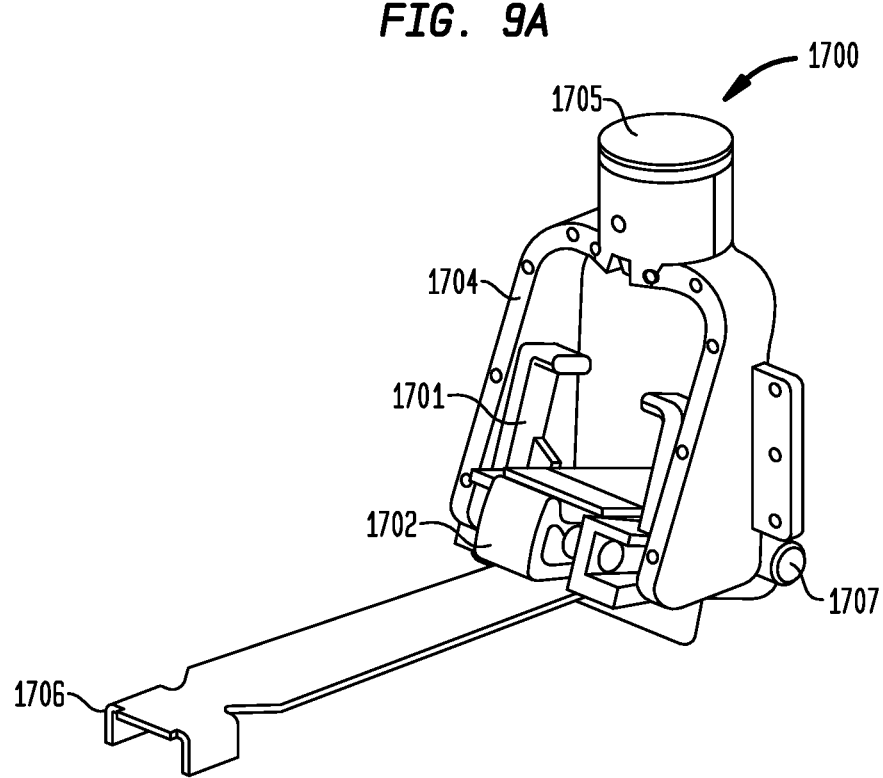
FIGS. 9A-G are schematic perspective, cross-sectional and side views of another example of a resheathing lock mechanism.
Figure 9B:
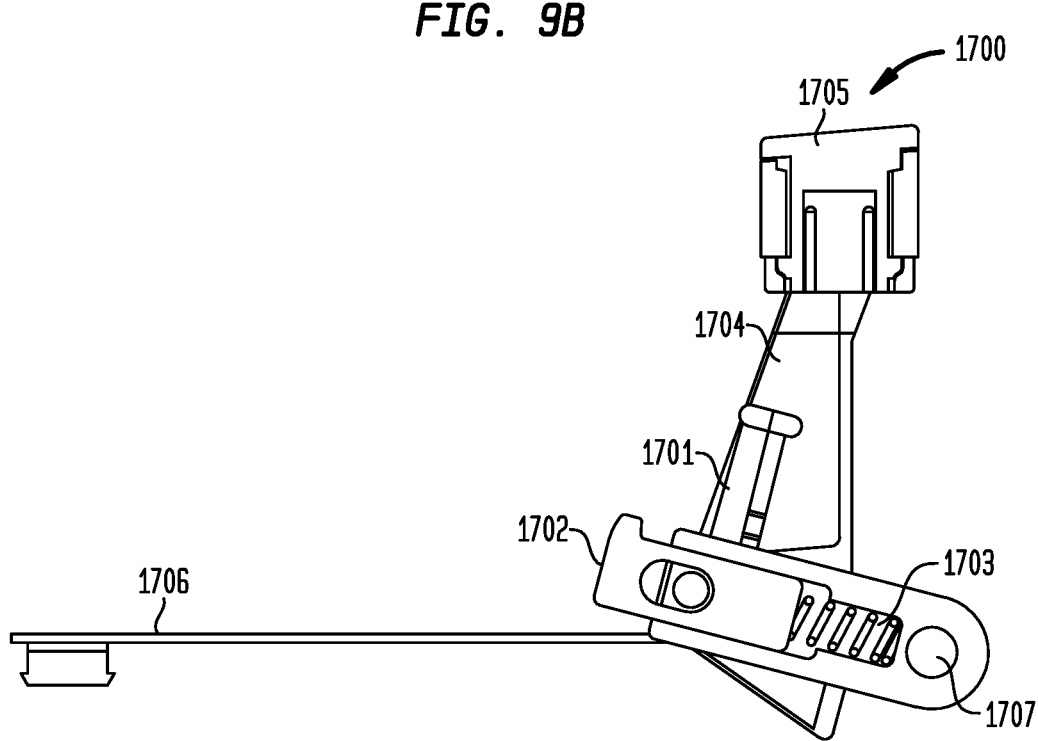

FIGS. 9A-G illustrate another example of a resheathing lock mechanism 1700. As shown in FIGS. 9A-B, resheathing lock mechanism 1700 generally includes a lock body 1701 having of two ribs that face one another and lock finger 1702 that sits on compression spring 1703 and protrudes from the lock body in the distal direction. Lock body 1701 is coupled to lock arms 1704, which in turn are coupled to a lock button 1705 that protrudes from frame 1030. A dowel hinge pin 1707 pivotally connects lock body 1701 to frame 1030. A leaf spring 1706 extending from the base of lock body 1701 and fixed to the frame 1030 is configured to apply a constant upward force to lock body 1701.

Figure 9C:
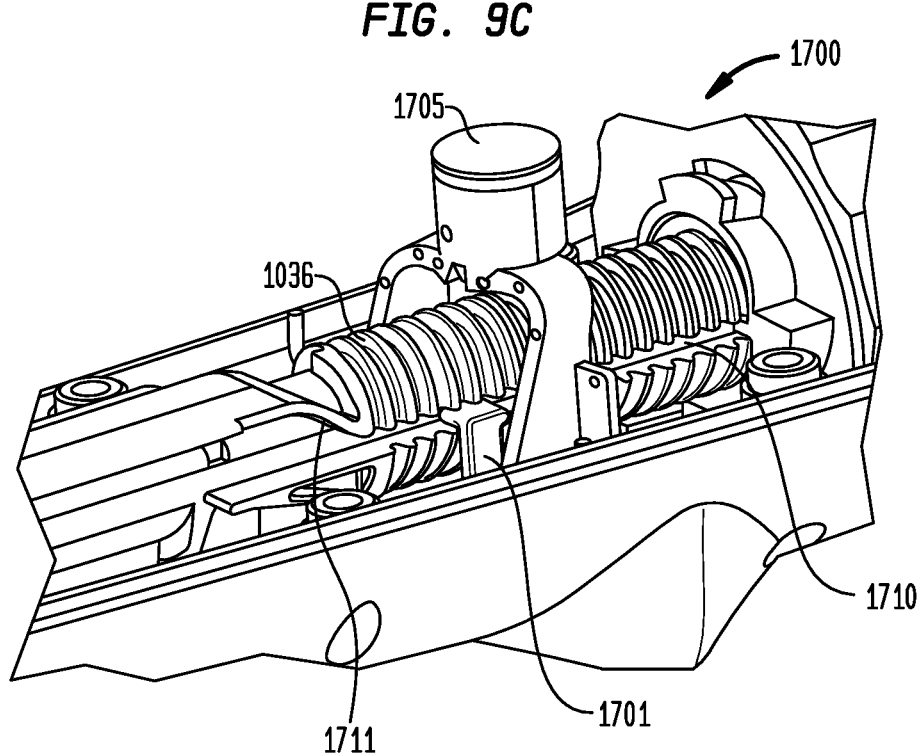
Figure 9D:
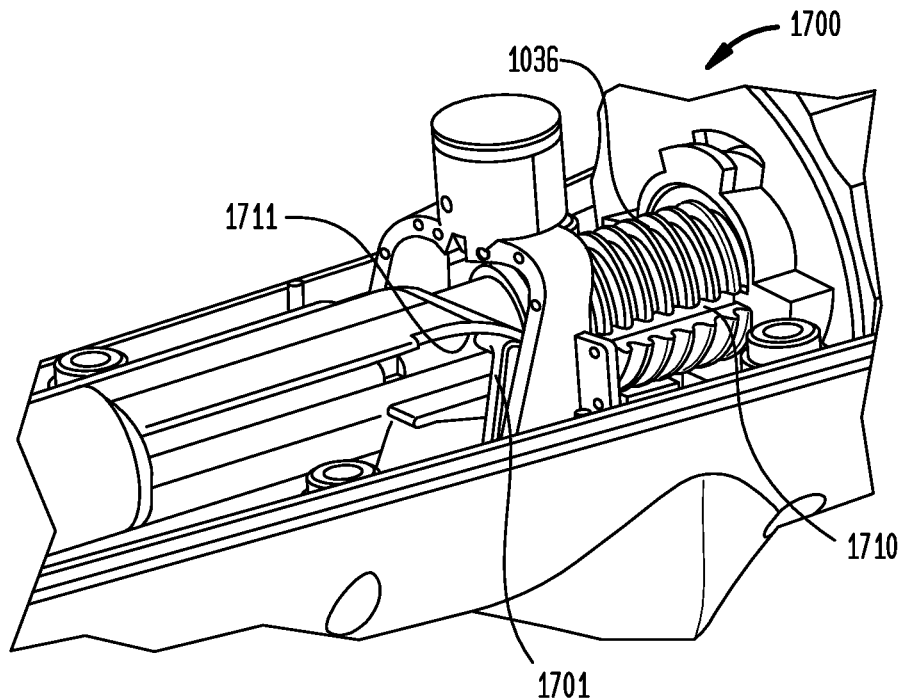

As shown in FIGS. 9C-D, ribs of the lock body 1701 are disposed in elongated slots 1710 formed on opposite sides of threaded rod 1036. As the actuator 1021 is operated to move carriage assembly 1040 with respect to lock mechanism 1700, the ribs ride along slots 1710 in the threaded rod 1036. At or near the distal end of the threaded rod 1036, each of the slots includes a ramp 1711 that angles upward toward the upper portion of frame 1030 (not shown). As the carriage assembly 1040 and threaded rod 1036 move proximally, the ribs of lock body 1701 continue to ride along the slots 1710 in threaded rod 1036 and up ramp 1711 as the lock body is urged to pivot upward by leaf spring 1706 (FIG. 9D).

Figure 9E:
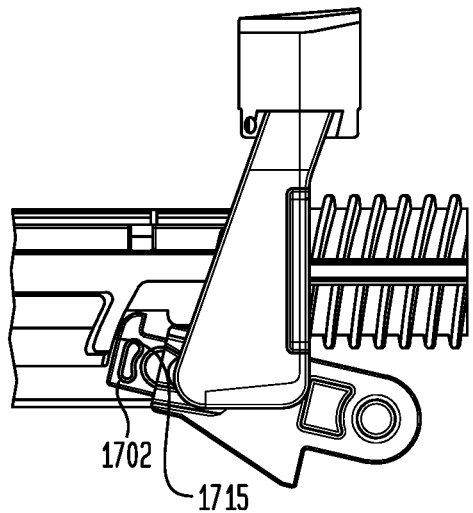
Figure 9F:
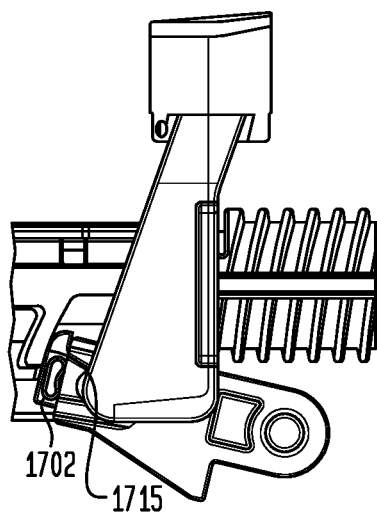
Figure 9G:
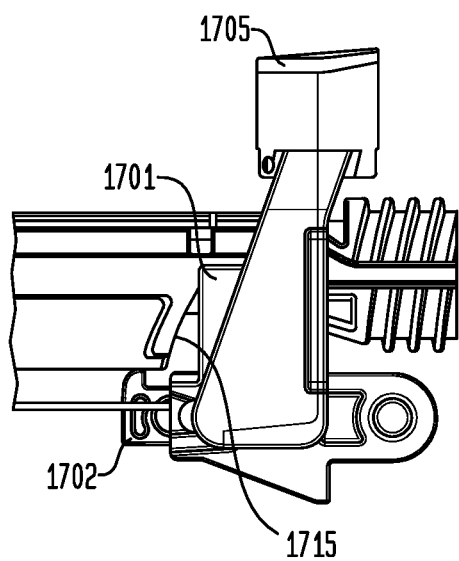

The upward movement of the lock body 1701 moves lock finger 1702 upward toward carriage assembly 1040, wherein it is eventually received in a cavity 1715 formed in the carriage assembly (FIG. 9E). As the carriage assembly continues to move proximally with rotation of the actuator 1021, lock finger 1702 contacts an end wall of cavity 1715 such that for the retraction of the carriage assembly gradually compresses spring 1703. When spring 1703 is fully compressed, carriage assembly 1040 is mechanically locked against further travel (FIG. 9F). This locked position corresponds to the point past which resheathing of the heart valve is no longer possible. The user may test functionality of the valve at this point, resheathe and re-implant the valve, or remove the prosthetic heart valve entirely. If the physician decides to continue the procedure and release the valve entirely, lock button 1705 may be depressed, pivoting the lock body 1701 and lock finger 1702 downward until lock finger 1702 no longer contacts the end wall of cavity 1715. At this point, spring 1703 may force lock finger 1702 outward and below carriage assembly 1040, releasing the carriage assembly for further proximal movement (FIG. 9G).

The actuator 1021 of the delivery device 1010 may also include a clutch mechanism so that when the resheathing lock 1700 is engaged, if the user continues to rotate the actuator a clutch between the actuator and the threaded rod 1036 prevents damage to the device. FIG. 10A shows one example of a clutch mechanism for use with actuator 1021. As shown, a clutch plate 1804 is assembled in a shell 1801 of actuator 1021 with a compression spring 1805 disposed between the clutch plate and the shell. In its assembled position, features (not shown) on the clutch plate 1804 engage with corresponding features (not shown) in the interior of shell 1801 to rotationally lock the clutch plate to the shell but permit the clutch plate to move axially within the shell. A drive nut 1803 is positioned adjacent clutch plate 1804, and the entire assembly is enclosed by a wheel cap 1802. A pair of assembly screws 1806 assemble the wheel cap 1802 to the wheel shell 1801 to hold the assembly together. Drive nut 1803 is internally threaded so that the fully assembled actuator 1021 may be threaded onto threaded rod 1036. Drive nut 1803 is not rotationally locked to shell 1801 but rather is freely rotatable relative to same. A cross-sectional view of the assembled actuator 1021 mounted on threaded rod 1036 is shown in FIG. 10B.

Details of drive nut 1803 and clutch plate 1804 will be described in greater detail with reference to FIGS. 10C and 10D. Drive nut 1803 includes a plurality of directional teeth 1813 around its circumference, each tooth having a sloped portion 1814 and a generally perpendicular portion 1815. The teeth 1813 on drive nut 1803 confront a plurality of complementary directional teeth 1816 positioned around the circumference of clutch plate 1804. Directional teeth 1816 have a similar configuration to the teeth 1813 of the drive nut 1803 so that the teeth are able to mesh with one another. When a predetermined axial force is reached upon rotation of the actuator 1021 in the deployment direction, teeth 1813 and 1816 slip relative to one another in a first direction. Compression spring 1805 applies a constant engagement force to keep clutch plate 1804 engaged with drive nut 1803 until the predetermined force is reached. Slippage occurs when a force greater than the predetermined force is applied, which typically occurs when the actuator is rotated while the resheathing lock mechanism 1700 is in the locked position. The predetermined slippage force may be determined by the angle of the sloped portion of teeth 1813 and 1816, the height of the teeth (i.e., the height of the perpendicular portions), spring force of compression spring 1805, and friction between drive nut 1803 and clutch plate 1804.

In use, resheathing lock mechanism 1700 may be urged toward the locked positon as described above, preventing the carriage assembly 1040 from moving further in the proximal direction. As carriage assembly 1040 is unable to move proximally, drive nut 1803 also will be unable to move as actuator 1021 is rotated in the direction causing proximal movement of the carriage assembly. The continued effort to rotate actuator 1021 will eventually result in the exerting of the predetermined force on the actuator. When this force is reached, the rotational force on the wheel shell 1801 will drive the clutch plate teeth 1816 up the sloped portion 1814 of the teeth of the drive nut 1803, moving the clutch plate 1804 axially until the teeth slip relative to one another. Thus, wheel shell 1801 will be allowed to rotate without any movement of carriage assembly 1040 and without exerting excessive force on the resheathing lock mechanism 1700 that could potentially damage same. In effect, this clutch mechanism serves to limit the amount of force that the user can apply to the resheathing lock mechanism 1700 and also provides a user input that the partial deployment limit has been reached when the user senses that the wheel is turning but no further actuation results. During re-sheathing of the valve, where the forces on the catheter are highest, in a direction opposite the first direction, the teeth are engaged in such a manner as to prevent any slippage of the clutch due to the presence of generally perpendicular portions 1815 on the teeth.

Figure 11A:
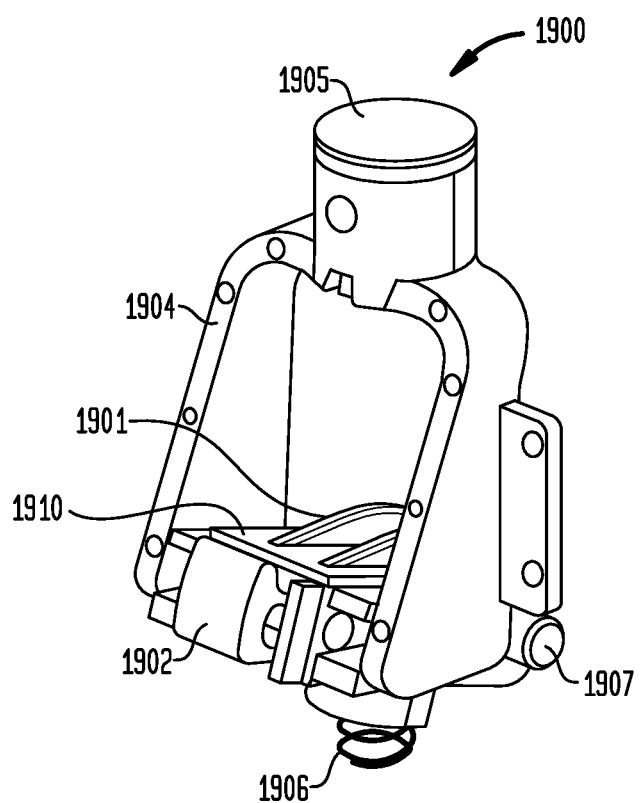
FIGS. 11A-E are schematic perspective, cross-sectional, front, and side views of another example of a resheathing lock mechanism.
Figure 11B:
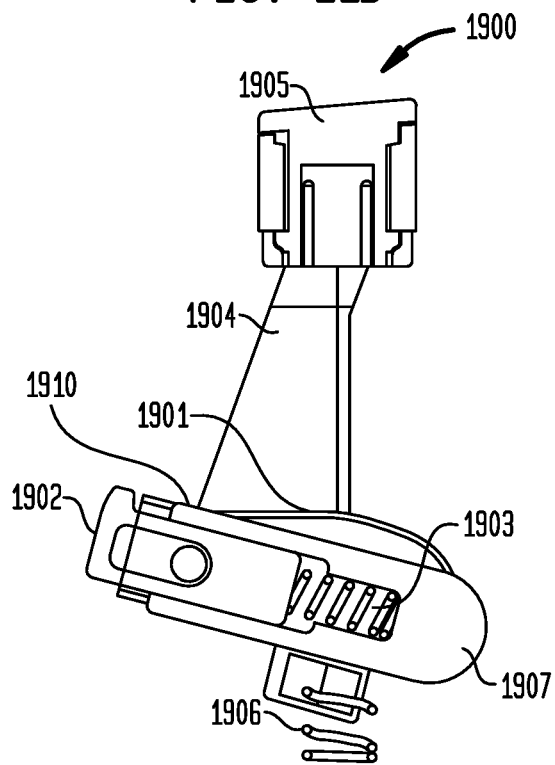

FIGS. 11A-E illustrate another example of a resheathing lock mechanism 1900, which is a variation of the resheathing lock mechanism 1700 shown in FIGS. 9A-G. The resheathing lock mechanism 1900 has an identical structure and function to the resheathing lock mechanism 1700, except for the differences that are described below. As shown in FIGS. 11A-B, resheathing lock mechanism 1900 generally includes a lock body 1910 having two ribs 1901 that face one another and lock finger 1902 that sits on compression spring 1903 and protrudes from the lock body in the distal direction. Lock body 1910 is coupled to lock arms 1904, which in turn are coupled to a lock button 1905 that is configured to protrude through an opening in frame 1030 when in a locked condition. A dowel hinge pin 1907 pivotally connects lock body 1910 to frame 1030. A compression spring 1906 (e.g., a coil spring) extending from the base of lock body 1910 and fixed to frame 1030 is configured to apply a constant upward force to lock body 1910. In some embodiments, a torsion spring may be used in place of compression spring 1906.

Figure 11E:
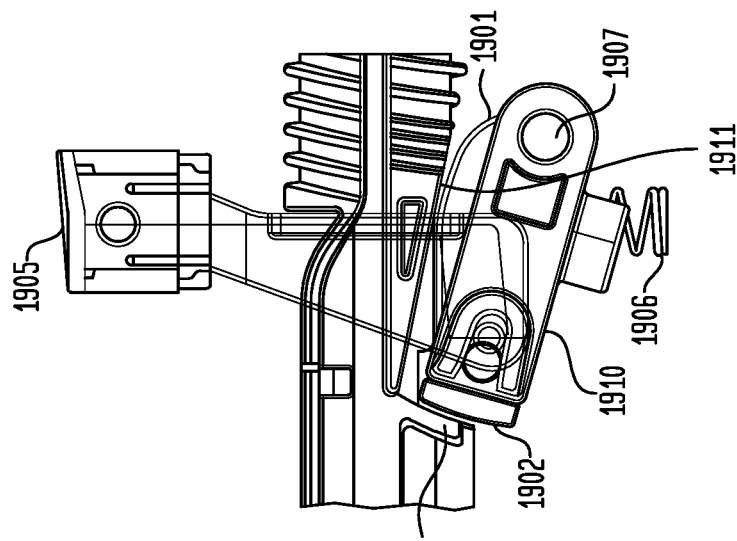
Figure 11D:
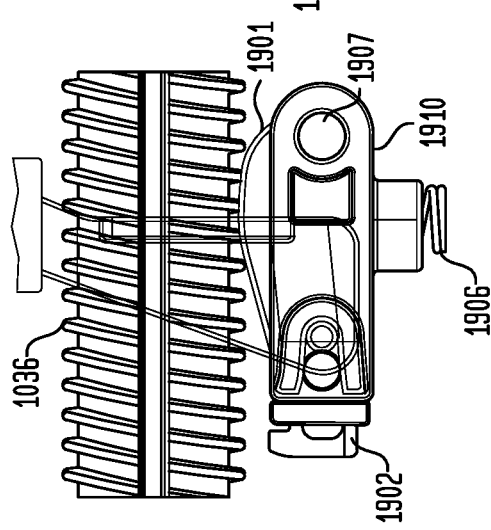
Figure 11C:
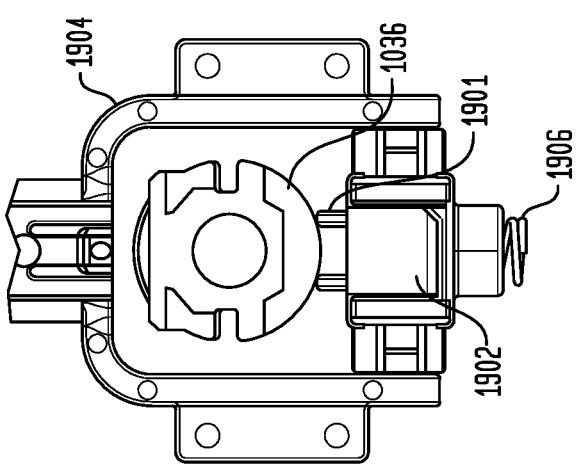

As shown in FIGS. 11C-D, ribs 1901 of the lock body 1910 maintain contact with the bottom of threaded rod 1036 due to the force provided by compression spring 1906. As actuator 1021 is operated to move carriage assembly 1040 and threaded rod 1036 with respect to lock mechanism 1900, the threads of the threaded rod slide along ribs 1901, with the ribs oriented transverse (e.g., 80°-85°) to the threads. At or near the distal end of threaded rod 1036, the threaded rod defines a cavity 1915 formed in the bottom of carriage assembly 1040. Cavity 1915 defines a ramp 1911 (FIG. 11E) that angles upward toward the upper portion of frame 1030 (not shown). As the carriage assembly 1040 and threaded rod 1036 move proximally, ribs 1901 of lock body 1910 continue to ride along the bottom of threaded rod 1036 and up ramp 1911 as the lock body is urged to pivot upward about dowel hinge pin 1907 by compression spring 1906.

The upward pivoting of the front of lock body 1910 moves lock finger 1902 upward toward carriage assembly 1040, wherein it is eventually received in cavity 1915. As carriage assembly 1040 continues to move proximally with the rotation of actuator 1021, lock finger 1902 contacts an end wall of cavity 1915 such that continued proximal translation of the carriage assembly gradually compresses spring 1903. When spring 1903 is fully compressed, carriage assembly 1040 is mechanically locked against further proximal travel (FIG. 11E). This locked position corresponds to the point past which resheathing of the heart valve is no longer possible. The user may test functionality of the valve at this point, resheathe and re-implant the valve, or remove the prosthetic heart valve entirely. If the physician decides to continue the procedure and release the valve entirely, lock button 1905 may be depressed, pivoting lock body 1910 and lock finger 1902 downward until the lock finger no longer contacts the end wall of cavity 1915. At this point, spring 1903 forces lock finger 1902 distally below carriage assembly 1040, releasing the carriage assembly for further proximal movement, in a manner similar to that shown in FIG. 9G.

In some examples, a delivery device for a collapsible prosthetic heart valve, the delivery device includes an inner shaft, a distal sheath disposed about a portion of the inner shaft to form a compartment with the inner shaft, the compartment being sized to receive the prosthetic heart valve, the inner shaft and the distal sheath being movable relative to one another, and a handle including a frame having a longitudinal axis, a deployment actuator operatively connected to the distal sheath, and a hub operatively connected to the inner shaft, each of the deployment actuator and the hub being independently capable of opening and closing the compartment, the hub further including a hub actuator coupled to the inner shaft; and/or the deployment actuator includes a first wheel having an axis of rotation disposed parallel to the longitudinal axis of the frame, and the hub actuator includes a second wheel having an axis of rotation that is parallel to the axis of rotation of the first wheel; and/or the second wheel is engaged with a translating cam having a threaded portion, the cam being coupled to the inner shaft; and/or the cam includes a flange that is perpendicular to the axis of rotation of the second wheel; and/or the cam is capable of translating between about 0.25 inches and about 1 inch in a direction parallel to the axis of rotation of the second wheel; and/or rotation of the second wheel results in longitudinally translating the inner shaft; and/or rotation of the deployment actuator results in longitudinally translating the distal sheath to cover or uncover the compartment.

In some examples, a delivery device for a collapsible prosthetic heart valve, the delivery device includes an inner shaft, a distal sheath disposed about a portion of the inner shaft to form a compartment sized to receive the prosthetic heart valve, the inner shaft and the distal sheath being movable relative to one another, and a handle including a frame having a longitudinal axis, a deployment actuator a resheathing lock having a lock body coupled to a protruding lock finger in contact with a compression spring, a lock arm coupled to the lock finger, and a lock button coupled to the lock arm; and/or the lock button has a first position disposed within the frame, and a second position in which the lock button protrudes from the frame; and/or the distal sheath is coupled to a threaded rod, the threaded rod being coupleable to the lock body; and/or the threaded rod includes a slot having a ramp and the lock body slides within the slot of the threaded rod; and/or the lock body has a pair of ribs configured to maintain contact with a bottom of the threaded rod when the threaded rod translates along the longitudinal axis of the frame; and/or the lock finger is configured to be disposed within a cavity of threaded rod in a first lock condition that prevents distal movement of the distal sheath, and to be substantially parallel with the threaded rod in a second unlocked condition that allows distal movement of the distal sheath; and/or the delivery device further includes a leaf spring coupled to the lock finger; and/or the leaf spring is configured to apply a force to the lock body; and/or the delivery device further includes a compression spring coupled to the lock finger; and/or the compression spring is configured to apply a force to the lock body.

In some examples, a delivery device for a collapsible prosthetic heart valve, the delivery device includes an inner shaft, a distal sheath disposed about a portion of the inner shaft to form a compartment sized to receive the prosthetic heart valve, the inner shaft and the distal sheath being movable relative to one another, and a handle including a frame having a longitudinal axis, and a deployment actuator operatively connected to the distal sheath, the deployment actuator including a clutch mechanism that rotationally couples the deployment actuator to the distal sheath in a first condition and rotationally decouples the deployment actuator from the distal sheath in a second condition; and/or the deployment actuator includes a wheel shell, and the clutch mechanism includes a clutch plate and a drive nut assembled within the wheel shell; and/or the drive nut includes a plurality of first teeth, each having a sloped portion; and/or the clutch plate includes a plurality of second teeth, complementary to the first teeth, the second teeth being meshed with the plurality of first teeth of the drive nut; and/or the assembly includes a compression spring disposed between the wheel shell and the clutch plate, the compression spring exerting a force pushing the clutch plate against the drive nut.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

It will be appreciated that the various dependent claims and the features set forth therein can be combined in different ways than presented in the initial claims. It will also be appreciated that the features described in connection with individual embodiments may be shared with others of the described embodiments.

The invention claimed is:

1. A delivery device for a collapsible prosthetic heart valve, the delivery device comprising:
   an inner shaft;
   a distal sheath disposed about a portion of the inner shaft to form a compartment with the inner shaft, the compartment being sized to receive the prosthetic heart valve, the inner shaft and the distal sheath being movable relative to one another; and
   a handle including a frame having a longitudinal axis, a deployment actuator operatively connected to the distal sheath, and a hub moveable relative to the frame between a proximal-most position where the hub is longitudinally spaced from the frame, and a distal-most position where the hub terminates proximal to a proximal end of the frame, the hub being operatively connected to the inner shaft, each of the deployment actuator and the hub being independently capable of opening and closing the compartment, the hub further including a hub wheel disposed within the hub and translatable therewith, the hub wheel being coupled to the inner shaft and being rotatable relative to the inner shaft.

2. The delivery device of claim 1, wherein the deployment actuator includes a first wheel having an axis of rotation disposed parallel to the longitudinal axis of the frame, and the hub wheel has an axis of rotation that is parallel to the axis of rotation of the first wheel.

3. The delivery device of claim 2, wherein the hub wheel is engaged with a translating cam having a threaded portion, the cam being coupled to the inner shaft.

4. The delivery device of claim 3, wherein the cam includes a flange that is perpendicular to the axis of rotation of the hub wheel.

5. The delivery device of claim 3, wherein the cam is capable of translating between about 0.050 inches and about 1 inch in a direction parallel to the axis of rotation of the hub wheel.

6. The delivery device of claim 3, wherein the cam is capable of translating between about 0.25 inches and about 1 inch in a direction parallel to the axis of rotation of the hub wheel.

7. The delivery device of claim 3, wherein rotation of the hub wheel results in longitudinally translating the inner shaft.

8. The delivery device of claim 1, wherein rotation of the deployment actuator results in longitudinally translating the distal sheath to cover or uncover the compartment.

9. The delivery device of claim 1, wherein the hub and the frame are decoupleable from one another.

10. The delivery device of claim 1, wherein the hub includes at least one first feature and the frame includes at least one second feature, the at least one first feature and the at least one second feature being coupleable to one another.

11. The delivery device of claim 1, wherein the hub includes at least one clip and the frame includes at least one void, the at least one clip being capable of mating within the at least one void.

12. The delivery device of claim 11, wherein the hub further includes at least one button configured to release the at least one clip from the at least one void.

13. The delivery device of claim 1, wherein the hub and the frame do not overlap along the longitudinal axis.

14. The delivery device of claim 1, wherein the hub wheel includes an exposed portion disposed outside the hub.

* * * * *